US012738361B2

(12) United States Patent
Bozarth et al.

(10) Patent No.: US 12,738,361 B2
(45) Date of Patent: Sep. 15, 2026

(54) PARALLEL PROCESSING SYSTEMS AND METHODS FOR REAL-TIME MULTIMODAL BEHAVIORAL CLASSIFICATION USING NEURAL NETWORKS WITH DYNAMIC CONTENT ADAPTATION

(71) Applicant: Center for Social Dynamics, LLC, Concord, CA (US)

(72) Inventors: Kelly Jean Bozarth, Corona Del Mar, CA (US); Gurpreet Kaur, Dublin, CA (US); Ashley Marie Stilley, Temecula, CA (US)

(73) Assignee: Center for Social Dynamics, LLC, Concord, CA (US)

( * ) Notice: Subject to any disclaimer, the term of this patent is extended or adjusted under 35 U.S.C. 154(b) by 0 days.

(21) Appl. No.: 19/432,740

(22) Filed: Dec. 24, 2025

(65) Prior Publication Data

US 2026/0188467 A1 Jul. 2, 2026

Related U.S. Application Data

(60) Provisional application No. 63/739,429, filed on Dec. 27, 2024.

(51) Int. Cl.
*G16H 20/70* (2018.01)

(52) U.S. Cl.
CPC .................................. *G16H 20/70* (2018.01)

(58) Field of Classification Search
CPC ..................................................... G16H 20/70
See application file for complete search history.

(56) References Cited

U.S. PATENT DOCUMENTS 4,860,214 A * 8/1989 Matsuda ................ G06F 18/25 706/53
5,722,418 A * 3/1998 Bro ....................... H04M 11/00 128/920
6,186,145 B1 * 2/2001 Brown ................... A63F 13/52 600/300

(Continued)

*Primary Examiner* — Michael I Ezewoko
(74) *Attorney, Agent, or Firm* — Carr & Ferrell LLP

(57) ABSTRACT

Parallel processing computer systems and methods for real-time multimodal behavioral classification and dynamic content adaptation are provided. A parallel processing pipeline implements concurrent execution of sensor data ingestion, neural network inference, content adaptation, and rendering stages across specialized processor resources including graphics processing units and tensor processing units. The parallel processing pipeline achieves end-to-end latency of less than 200 milliseconds from sensor data capture to rendered content output, representing a reduction of at least 60% compared to conventional sequential architectures. A trained neural network model comprising feature extraction modules with parallel convolutional branches, a bidirectional Long Short-Term Memory temporal processing module, and a classification module processes multimodal sensor data including video frame data, audio waveform data, motion tracking data, and physiological sensor data to classify behavioral states and calculate engagement levels. A dynamic adjustment algorithm modifies content parameters based on real-time performance metrics.

27 Claims, 7 Drawing Sheets

(56) References Cited

U.S. PATENT DOCUMENTS 6,425,764 B1 * 7/2002 Lamson ................ G16H 30/40 434/236
6,569,093 B2 * 5/2003 Iliff ....................... G16H 70/60 128/920
6,957,202 B2 * 10/2005 Skaanning .............. G06N 7/01 706/55
7,043,439 B2 * 5/2006 Jost .................. G06F 16/90332 707/E17.139
7,155,421 B1 * 12/2006 Haldar .................... G06N 5/01 706/46
7,311,666 B2 * 12/2007 Stupp .................... G16H 50/30 128/920
7,958,066 B2 * 6/2011 Pinckney .............. G06N 20/00 707/706
7,974,872 B2 * 7/2011 Katayama .......... G06Q 30/0201 705/26.7
8,024,332 B2 * 9/2011 Cao ...................... G06F 16/338 707/728
8,655,817 B2 * 2/2014 Hasey ................... G16H 50/30 706/45
8,834,174 B2 * 9/2014 Malik ..................... A61B 5/16 434/236
9,305,059 B1 * 4/2016 Glickman ........... G06F 16/2457
9,443,199 B2 * 9/2016 Pinckney .............. G06Q 30/02
9,443,205 B2 * 9/2016 Wall ...................... A61B 5/168
10,311,645 B1 * 6/2019 Ravindran ............ A61B 5/163
10,478,112 B2 * 11/2019 Wall ...................... A61B 5/168
10,984,899 B2 * 4/2021 Vaughan ............. A61B 5/7267
11,176,444 B2 * 11/2021 Wall ...................... G06N 20/00
11,266,338 B1 * 3/2022 Tao ...................... A61B 5/1128
11,538,355 B2 * 12/2022 Juliano ................... G06F 3/012
11,862,339 B2 * 1/2024 Wall ...................... A61B 5/168
11,972,336 B2 * 4/2024 Vaughan ................. G06N 3/08
11,978,555 B2 * 5/2024 Sobol ...................... H04W 4/38
12,205,725 B2 * 1/2025 Vaughan ................ G16H 50/20
12,383,179 B2 * 8/2025 Davis ............... A61B 5/150824
12,402,840 B2 * 9/2025 Vaughan ................ G16H 10/20
12,564,342 B2 * 3/2026 Abbas .................... A61B 5/165
2001/0034615 A1 * 10/2001 Wilkinson ............. G16H 80/00 705/2
2001/0036444 A1 * 11/2001 Placke .................... A61P 35/00 424/649
2002/0002325 A1 * 1/2002 Iliff ....................... G16H 50/20 600/300
2002/0019747 A1 * 2/2002 Ware ..................... G16H 50/20 705/2
2002/0035486 A1 * 3/2002 Huyn ....................... G09B 7/02 705/3
2002/0042786 A1 * 4/2002 Scarborough ............ G09B 7/02 706/21
2003/0032069 A1 * 2/2003 Muraca .................. G16B 25/30 702/19
2003/0191680 A1 * 10/2003 Dewar ........... G06Q 10/063112 706/45
2004/0015337 A1 * 1/2004 Thomas ................. G16H 50/20 703/11
2004/0103001 A1 * 5/2004 Mazar .................... G16H 50/50 600/300
2004/0147840 A1 * 7/2004 Duggirala ............. G06T 7/0012 600/437
2004/0197750 A1 * 10/2004 Donaher .................. G09B 7/00 434/236
2004/0265784 A1 * 12/2004 Stout ........................ G09B 7/00 434/433
2005/0075887 A1 * 4/2005 Bernard ................ G10L 15/063 704/277
2005/0142524 A1 * 6/2005 Simon .................... G16H 10/20 434/362
2005/0176057 A1 * 8/2005 Bremer .............. G01N 33/5082 435/6.16
2005/0187802 A1 * 8/2005 Koeppel ................ G06Q 40/06 705/4
2005/0197988 A1 * 9/2005 Bublitz .............. G06Q 30/0201 706/46
2005/0209785 A1 * 9/2005 Wells ..................... G16B 40/30 702/19
2005/0216243 A1 * 9/2005 Graham ................. G16H 40/67 703/11
2005/0260549 A1 * 11/2005 Feierstein ................ G09B 7/02 434/236
2006/0009683 A1 * 1/2006 Sakai ....................... A61B 5/00 600/300
2006/0059145 A1 * 3/2006 Henschke .............. G16H 10/60
2006/0078856 A1 * 4/2006 Kellman .................. G09B 7/00 434/118
2006/0282306 A1 * 12/2006 Thissen-Roe ............................... G06Q 10/063112 705/7.14
2007/0118399 A1 * 5/2007 Avinash ................. G16H 10/60 705/2
2007/0207449 A1 * 9/2007 Feierstein ................ G09B 7/02 434/323
2008/0014566 A1 * 1/2008 Chapman ............... G16H 70/60 434/262
2008/0016024 A1 * 1/2008 Andoh ................... G06Q 30/02
2009/0007924 A1 * 1/2009 Iliff ....................... G16H 50/20 600/300
2009/0016559 A1 * 1/2009 Cleary ................. H04R 1/1091 381/378
2009/0083075 A1 * 3/2009 Henschke .............. G16H 10/60 705/3
2009/0137923 A1 * 5/2009 Suffin ................... A61B 5/4076 600/300
2009/0182578 A1 * 7/2009 Ozersky ........... G06Q 10/06375 600/300
2009/0259494 A1 * 10/2009 Feder ....................... G06N 7/01 705/2
2010/0023346 A1 * 1/2010 Paty ................... G06Q 30/0203 705/2
2010/0068687 A1 * 3/2010 Bertelsen ................. G09B 7/02 434/322
2010/0177950 A1 * 7/2010 Donovan ............... G16H 50/30 702/19
2010/0179928 A1 * 7/2010 Hodgin .................... G06N 5/04 706/46
2010/0184093 A1 * 7/2010 Donovan ............... G16B 25/00 435/287.1
2010/0189818 A1 * 7/2010 Tsai ...................... A61K 31/16 514/474
2010/0280760 A1 * 11/2010 Pi .......................... G16H 50/20 436/87
2011/0082712 A1 * 4/2011 Eberhardt, III ......... G16Z 99/00 705/4
2011/0119212 A1 * 5/2011 De Bruin ............... A61B 5/369 706/12
2011/0145161 A1 * 6/2011 Scarborough ...... G06Q 10/0639 705/321
2011/0184379 A1 * 7/2011 Van Antwerp ......... G16H 70/20 604/503
2012/0004925 A1 * 1/2012 Braverman ............ G06Q 10/00 706/46
2012/0059282 A1 * 3/2012 Agichtein .............. A61B 5/165 600/587
2012/0101852 A1 * 4/2012 Albert .................... G06Q 40/08 705/4
2012/0102405 A1 * 4/2012 Zuckerman ............ G16H 50/20 715/733
2012/0108909 A1 * 5/2012 Slobounov ............... A61B 5/16 600/300
2012/0270199 A1 * 10/2012 Malik .................... A61B 5/165 702/19
2013/0159010 A1 * 6/2013 Paty ....................... G16Z 99/00 705/2
2013/0178731 A1 * 7/2013 Bosl ..................... A61B 5/7275 600/300
2013/0184603 A1 * 7/2013 Rothman ............. A61B 5/6803 600/544

(56) References Cited

U.S. PATENT DOCUMENTS

2013/0184792 A1* 7/2013 Simon .................. A61N 1/0408 607/115
2013/0262357 A1* 10/2013 Amarasingham ...... G16H 50/70 706/21
2013/0267441 A1* 10/2013 Momeni ................. A61P 25/00 435/7.1
2014/0006319 A1* 1/2014 Anand ..................... G06N 5/02 706/46
2014/0052474 A1* 2/2014 Madan ................... G16H 50/50 705/3
2014/0063236 A1* 3/2014 Shreve ................. G06V 40/174 382/197
2014/0074848 A1* 3/2014 Kettunen .............. G06F 16/285 707/740
2014/0122109 A1* 5/2014 Ghanbari ............... G16H 10/20 705/2
2014/0141983 A1* 5/2014 Singh ................. A61K 39/3955 506/7
2014/0219986 A1* 8/2014 Greene .................. A61K 38/47 424/94.61
2014/0279746 A1* 9/2014 De Bruin ............... G16H 50/70 706/46
2014/0304200 A1* 10/2014 Wall .......................... G06F 8/30 706/12
2014/0336539 A1* 11/2014 Torres .................... A61B 5/162 600/595
2015/0004588 A1* 1/2015 Vats ......................... G09B 7/02 434/350
2015/0006192 A1* 1/2015 Sudharsan ............. G16H 40/67 705/2
2015/0080671 A1* 3/2015 Christensen ........... A61B 5/369 600/301
2015/0099946 A1* 4/2015 Sahin ....................... A61B 7/04 600/301
2015/0119437 A1* 4/2015 Clark ..................... A61K 47/62 514/401
2015/0154372 A1* 6/2015 Soenksen ............... G16H 50/30 705/2
2015/0197543 A1* 7/2015 Glass ...................... A61P 25/18 548/537
2015/0315182 A1* 11/2015 Lee ...................... C07D 403/12 514/249
2016/0046990 A1* 2/2016 Hensel ................. C12Q 1/6883 506/9
2016/0135706 A1* 5/2016 Sullivan ............... A61B 5/7267 600/509
2016/0140859 A1* 5/2016 Jiao ........................ G16H 50/30 434/362
2016/0180248 A1* 6/2016 Regan ...................... G09B 5/00 706/12
2016/0203280 A1* 7/2016 Neville .................... G06N 7/01 706/52
2016/0209428 A1* 7/2016 Naviaux ............ G01N 33/6848
2016/0342756 A1* 11/2016 Wall ..................... A61B 5/7267
2016/0357924 A1* 12/2016 Jenkins ................ A61B 5/4833
2017/0035792 A1* 2/2017 Montagnier ....... A61K 31/4196
2017/0069216 A1* 3/2017 Vaughan ................ G16H 50/30
2017/0091423 A1* 3/2017 Kumar ................... G16H 20/60
2017/0160878 A1* 6/2017 Endo .................... A61B 5/7264
2017/0262609 A1* 9/2017 Perlroth ................. G16H 10/60
2018/0098724 A1* 4/2018 Lu ........................ A61B 5/7264
2018/0184964 A1* 7/2018 Simon ....................... G06F 1/14
2018/0366144 A1* 12/2018 Ashoori ................. G16H 40/63
2019/0019581 A1* 1/2019 Vaughan ................ G16H 50/70
2019/0038202 A1* 2/2019 Wall ....................... A61B 5/168
2019/0043610 A1* 2/2019 Vaughan .............. A61B 5/4088
2019/0043618 A1* 2/2019 Vaughan ................ G16H 20/10
2019/0043619 A1* 2/2019 Vaughan ................ G16H 50/20
2019/0088366 A1* 3/2019 Vaughan ................ A61B 5/486
2019/0244127 A1* 8/2019 Amado ..................... A63F 9/24
2021/0133509 A1* 5/2021 Wall ...................... G16H 50/20

* cited by examiner

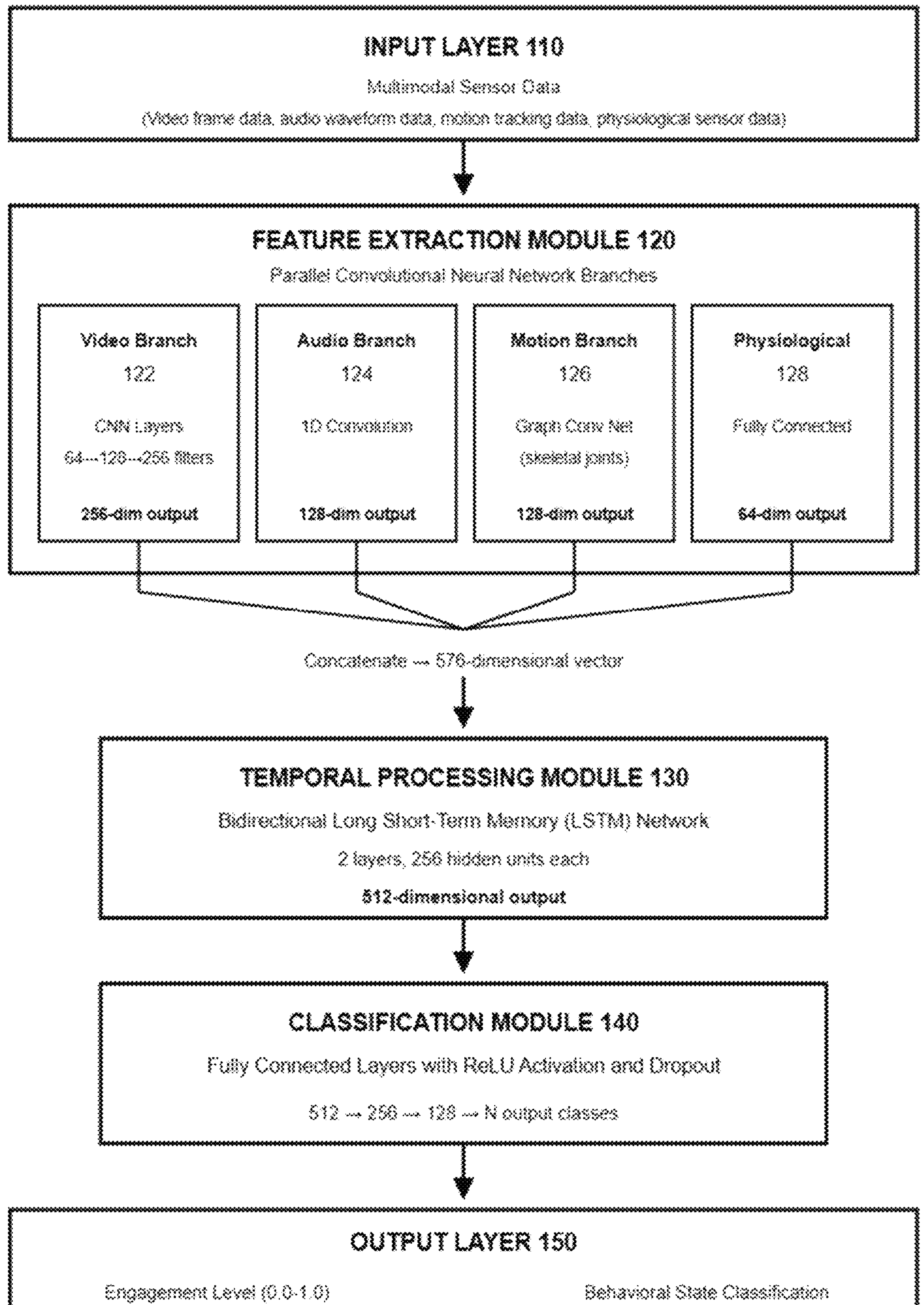
FIGURE 1
Neural Network Architecture 100
INPUT LAYER 110
Multimodal Sensor Data
(Video frame data, audio waveform data, motion tracking data, physiological sensor data)
FEATURE EXTRACTION MODULE 120
Parallel Convolutional Neural Network Branches
Video Branch
122
CNN Layers
64→128→256 filters
256-dim output
Audio Branch
124
1D Convolution
128-dim output
Motion Branch
126
Graph Conv Net
(skeletal joints)
128-dim output
Physiological
128
Fully Connected
64-dim output
Concatenate → 576-dimensional vector
TEMPORAL PROCESSING MODULE 130
Bidirectional Long Short-Term Memory (LSTM) Network
2 layers, 256 hidden units each
512-dimensional output
CLASSIFICATION MODULE 140
Fully Connected Layers with ReLU Activation and Dropout
512 → 256 → 128 → N output classes
OUTPUT LAYER 150
Engagement Level (0.0-1.0)
Sigmoid activation
Behavioral State Classification
Softmax activation

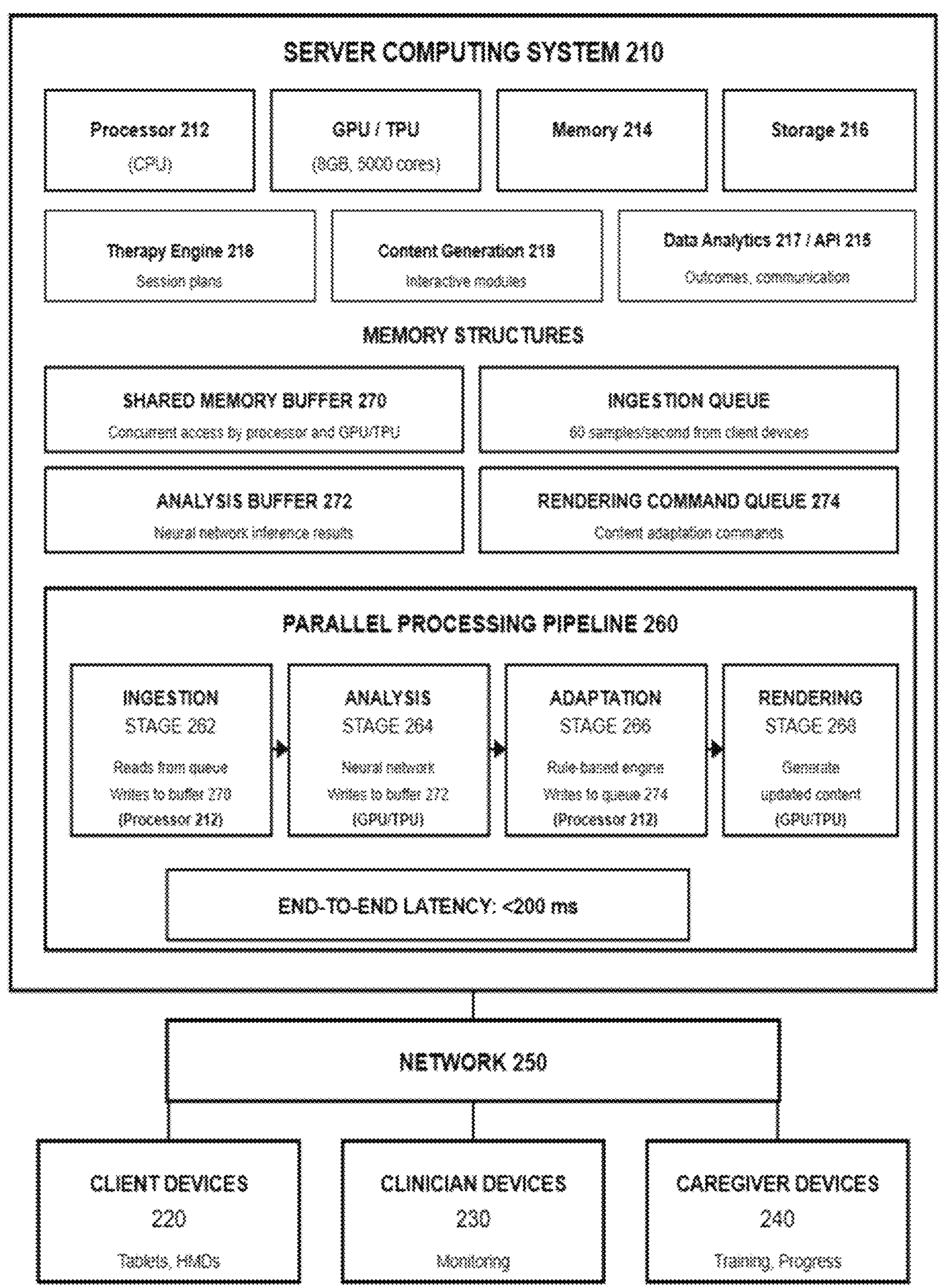
FIGURE 2
System Architecture 200
SERVER COMPUTING SYSTEM 210
Processor 212
(CPU)
GPU / TPU
(8GB, 5000 cores)
Memory 214
Storage 216
Therapy Engine 218
Session plans
Content Generation 219
Interactive modules
Data Analytics 217 / API 215
Outcomes, communication
MEMORY STRUCTURES
SHARED MEMORY BUFFER 270
Concurrent access by processor and GPU/TPU
INGESTION QUEUE
60 samples/second from client devices
ANALYSIS BUFFER 272
Neural network inference results
RENDERING COMMAND QUEUE 274
Content adaptation commands
PARALLEL PROCESSING PIPELINE 260
INGESTION
STAGE 262
Reads from queue
Writes to buffer 270
(Processor 212)
ANALYSIS
STAGE 264
Neural network
Writes to buffer 272
(GPU/TPU)
ADAPTATION
STAGE 266
Rule-based engine
Writes to queue 274
(Processor 212)
RENDERING
STAGE 268
Generate
updated content
(GPU/TPU)
END-TO-END LATENCY: <200 ms
NETWORK 250
CLIENT DEVICES
220
Tablets, HMDs
CLINICIAN DEVICES
230
Monitoring
CAREGIVER DEVICES
240
Training, Progress

FIGURE 3
Training Method 300 and Iterative Training Algorithm 350
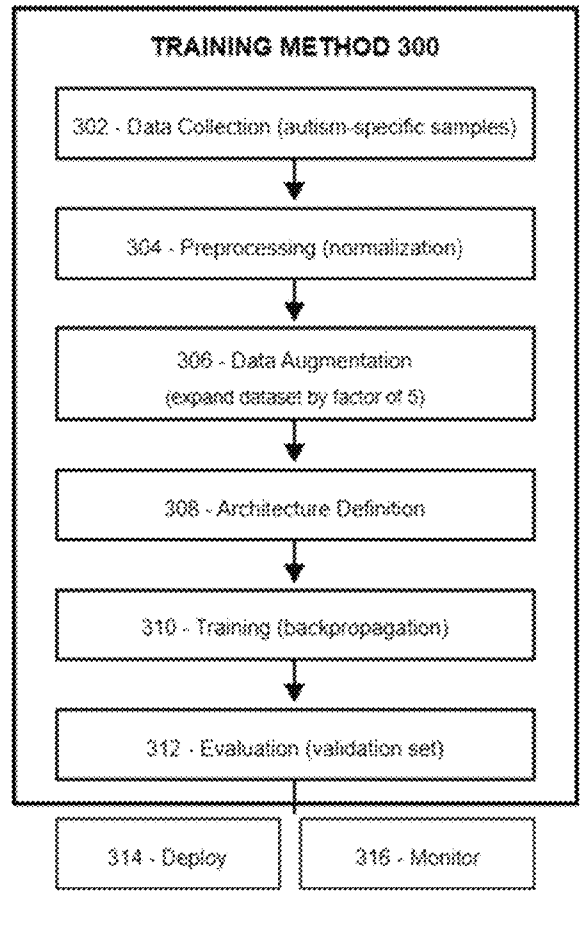
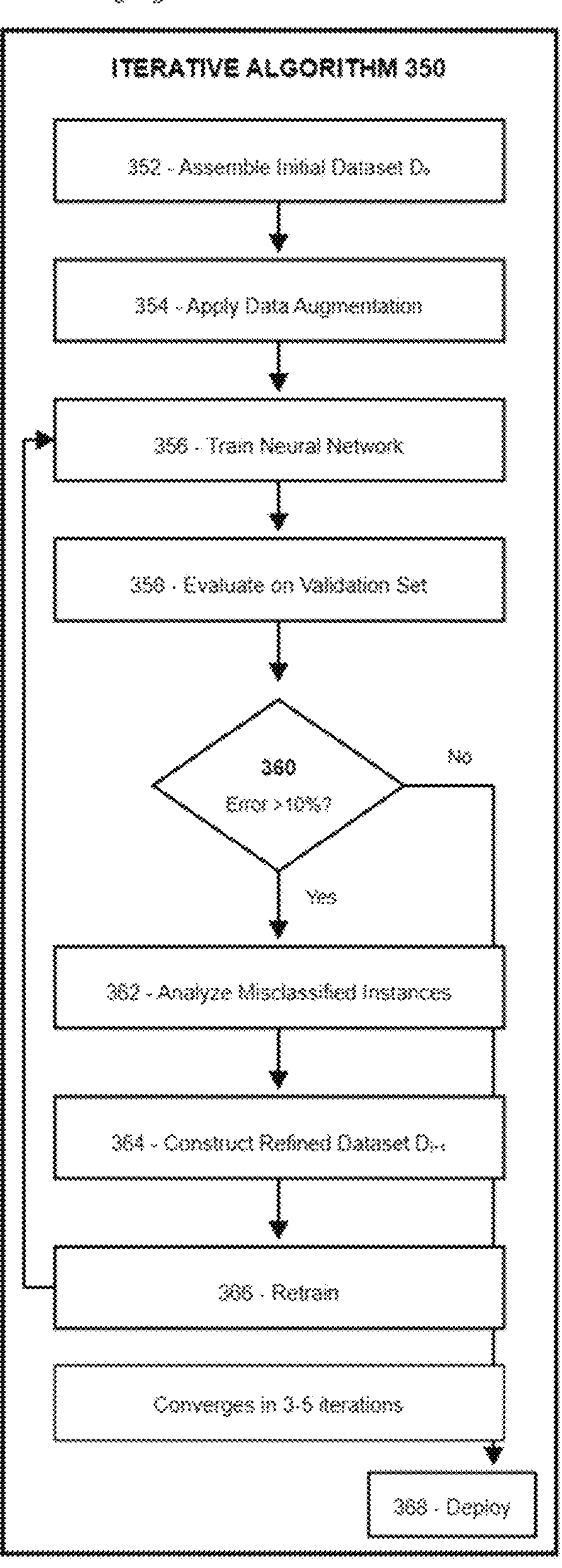
DATA AUGMENTATION
Random cropping of video frames
Horizontal flipping of video frames
Time stretching of audio (0.8-1.2×)
Background noise addition
Random rotation of motion data Immersive Therapy System 400

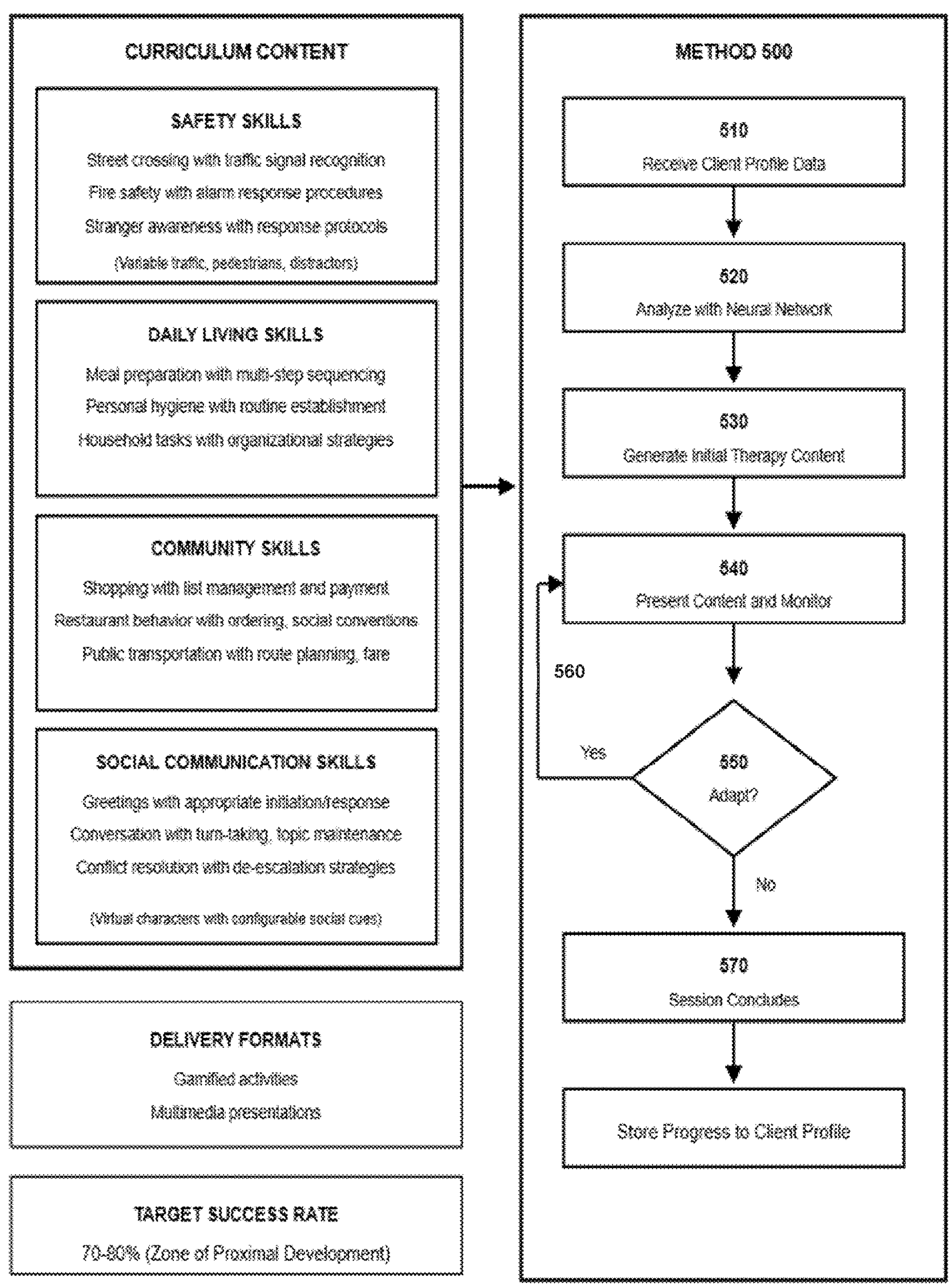
FIGURE 5
Curriculum Content and Dynamic Content Generation Method 500
CURRICULUM CONTENT
SAFETY SKILLS
Street crossing with traffic signal recognition
Fire safety with alarm response procedures
Stranger awareness with response protocols
(Variable traffic, pedestrians, distractors)
DAILY LIVING SKILLS
Meal preparation with multi-step sequencing
Personal hygiene with routine establishment
Household tasks with organizational strategies
COMMUNITY SKILLS
Shopping with list management and payment
Restaurant behavior with ordering, social conventions
Public transportation with route planning, fare
SOCIAL COMMUNICATION SKILLS
Greetings with appropriate initiation/response
Conversation with turn-taking, topic maintenance
Conflict resolution with de-escalation strategies
(Virtual characters with configurable social cues)
DELIVERY FORMATS
Gamified activities
Multimedia presentations
TARGET SUCCESS RATE
70-80% (Zone of Proximal Development)
METHOD 500
510
Receive Client Profile Data
520
Analyze with Neural Network
530
Generate Initial Therapy Content
540
Present Content and Monitor
560
Yes
550
Adapt?
No
570
Session Concludes
Store Progress to Client Profile

FIGURE 6
Telehealth Platform 600 and Caregiver Training Method 680
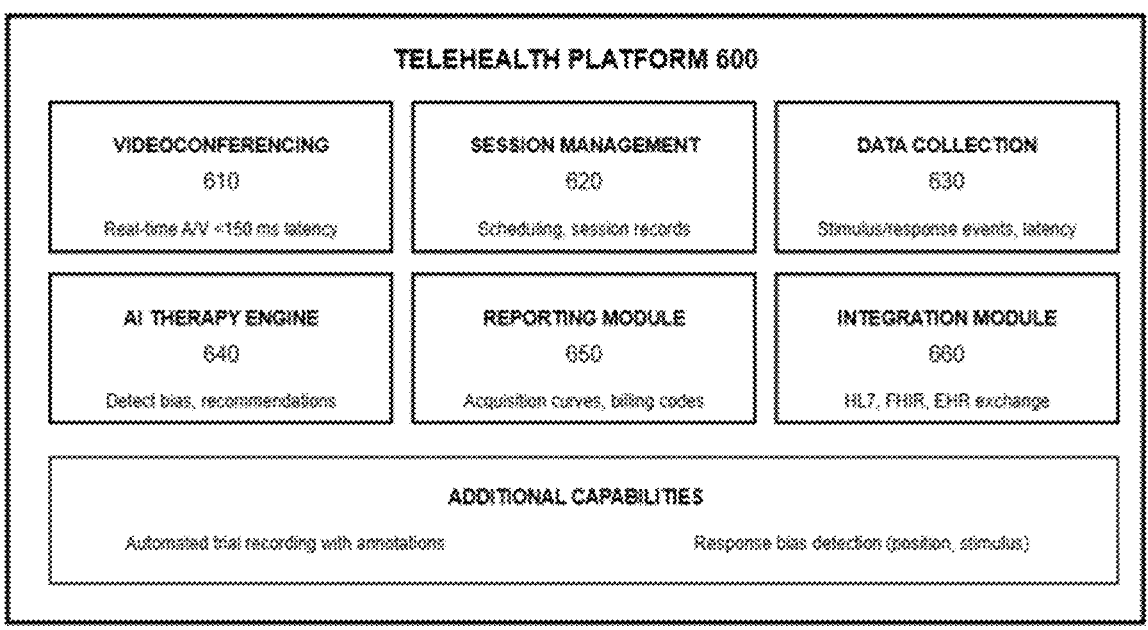
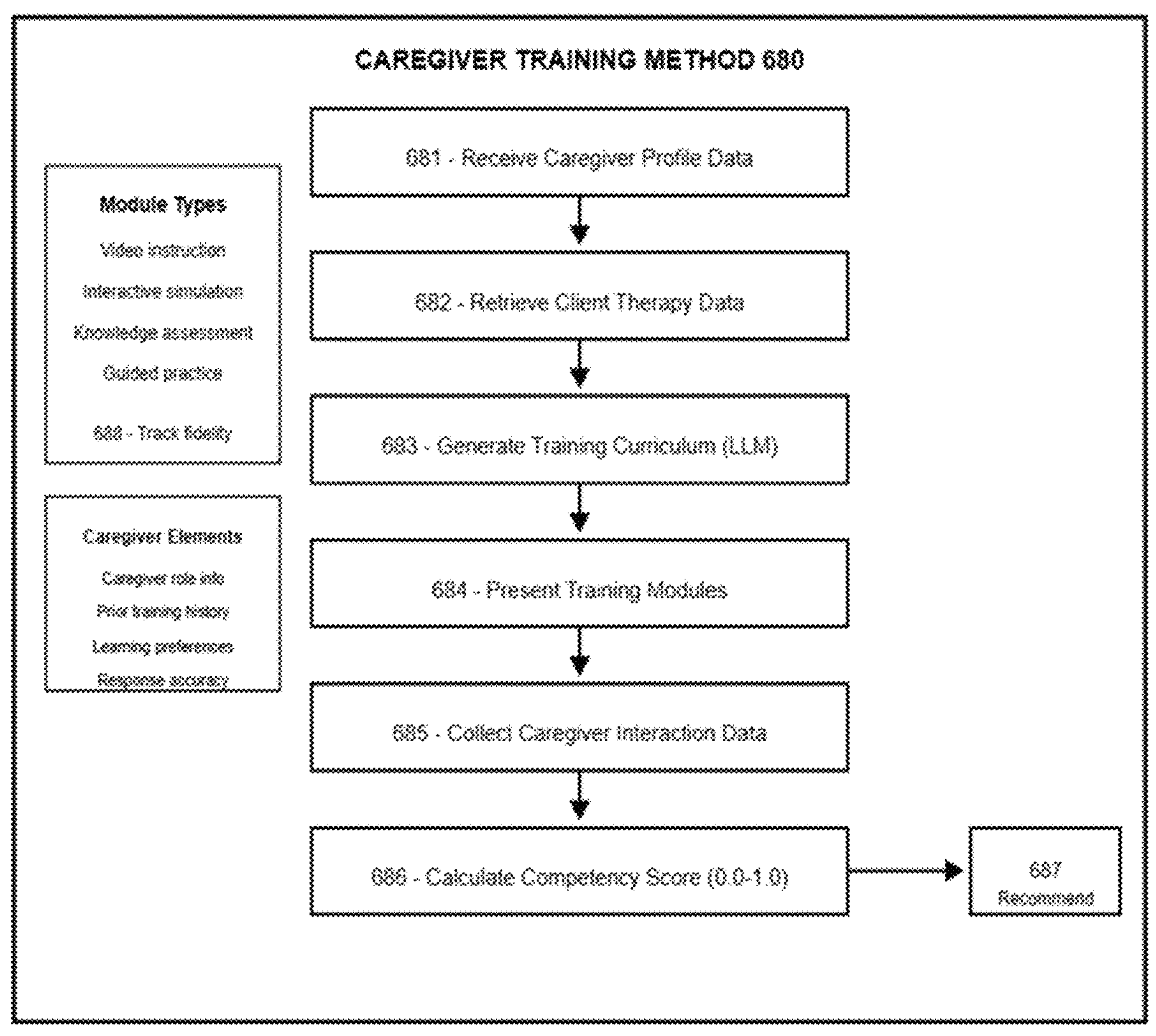

FIGURE 7
Data Integration and Dynamic Difficulty Adjustment
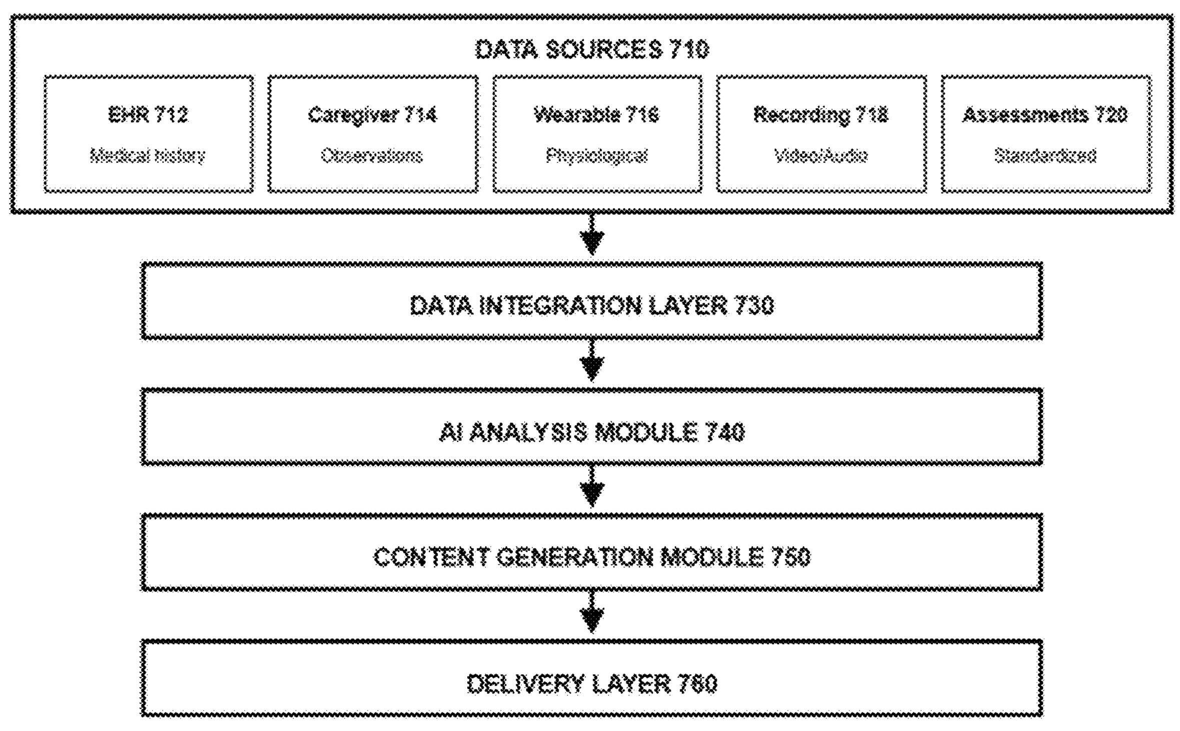
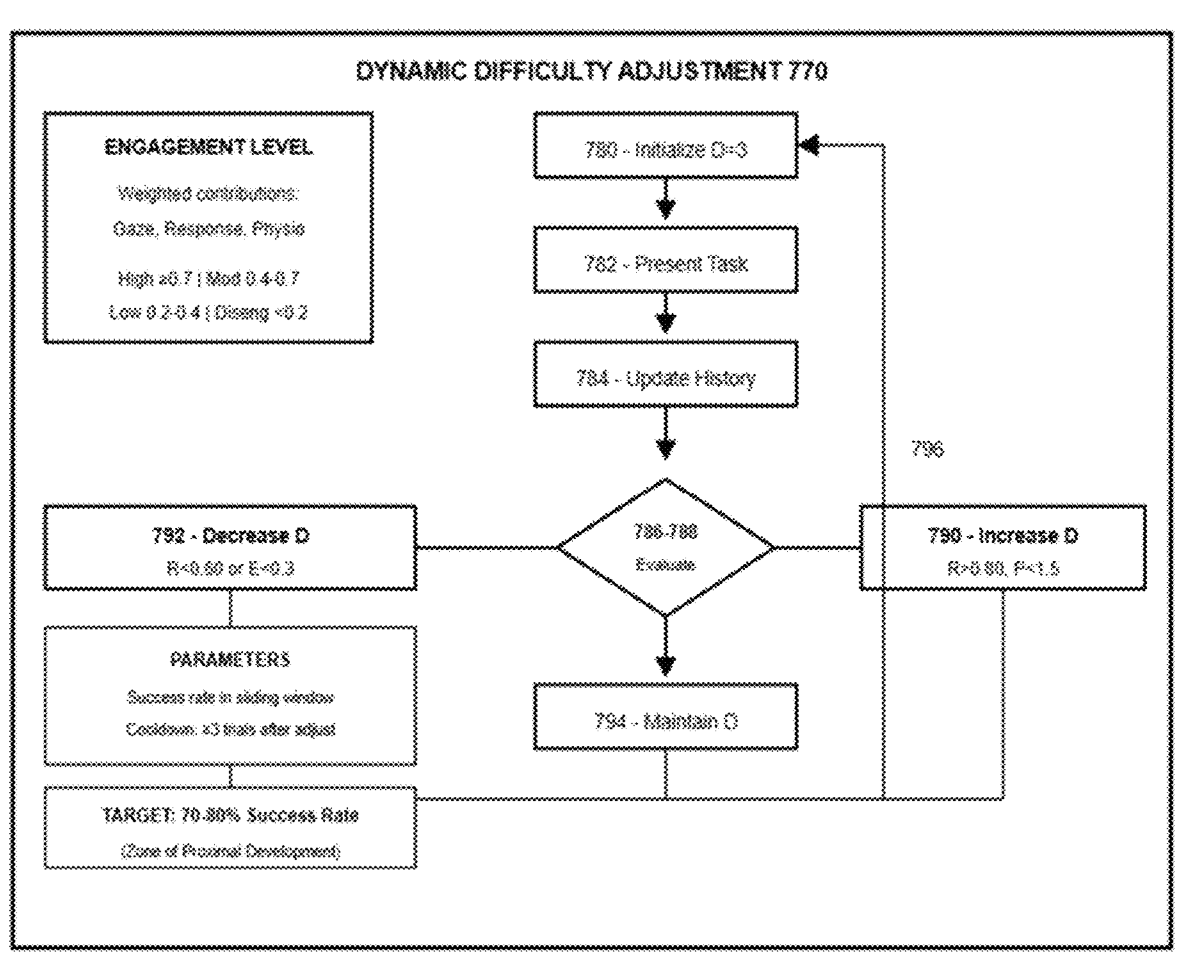

PARALLEL PROCESSING SYSTEMS AND METHODS FOR REAL-TIME MULTIMODAL BEHAVIORAL CLASSIFICATION USING NEURAL NETWORKS WITH DYNAMIC CONTENT ADAPTATION

CROSS-REFERENCE TO RELATED APPLICATIONS

This application claims the benefit of U.S. Provisional Patent Application Ser. No. 63/739,429, filed Dec. 27, 2024, the entire disclosure of which is incorporated herein by reference.

STATEMENT REGARDING FEDERALLY SPONSORED RESEARCH OR DEVELOPMENT

Not applicable.

FIELD OF THE DISCLOSURE

The present disclosure pertains to parallel processing computer architectures and neural network systems for real-time multimodal sensor data fusion, behavioral state classification, and dynamic content generation. The exemplary embodiments integrate specialized processor resources including graphics processing units, tensor processing units, and neural processing units executing concurrent processing pipelines to achieve sub-200-millisecond end-to-end latency from sensor data capture to adaptive content output. Applications include interactive training systems, immersive simulation environments, and adaptive learning platforms.

TECHNICAL FIELD

The present disclosure relates generally to computer systems and, more particularly, to specialized computing architectures that integrate neural network processors, sensor fusion systems, and immersive display technologies to solve technical problems in real-time behavioral data processing and adaptive content generation for therapeutic applications.

SUMMARY OF EXEMPLARY EMBODIMENTS

The following presents a simplified summary to provide a basic understanding of some exemplary embodiments. This summary is not an extensive overview and is not intended to identify key or critical elements or to delineate the scope of such embodiments. Its purpose is to present some concepts in a simplified form as a prelude to the more detailed description that is presented later. In accordance with one exemplary embodiment, a computer-implemented method for delivering adaptive therapy sessions is provided. The method comprises receiving, by at least one processor, client-specific data comprising at least one of behavioral assessment data, historical therapy session data, caregiver-reported observations, or skill acquisition metrics. The method further comprises analyzing, by the at least one processor executing a trained neural network model, the client-specific data to generate a personalized therapy session plan. The method additionally comprises dynamically adjusting, by the at least one processor, one or more parameters of the personalized therapy session plan in real time based on client performance data collected during execution of the therapy session. The method also comprises generating, by the at least one processor, at least one interactive learning module selected from gamified activities, multimedia presentations, or simulated real-world scenarios based on the personalized therapy session plan. The method further comprises outputting, by the at least one processor, the at least one interactive learning module for presentation to a client via at least one of an augmented reality display device, a virtual reality display device, or a computing device display.

In accordance with another exemplary embodiment, a system for providing artificial intelligence-driven Applied Behavior Analysis therapy is provided. The system comprises at least one processor and at least one non-transitory computer-readable medium storing instructions that, when executed by the at least one processor, cause the system to perform operations. The operations comprise receiving client behavioral data from a plurality of data sources including at least one of electronic health records, caregiver input interfaces, wearable sensor devices, or session recording systems. The operations further comprise processing the client behavioral data using a large language model to generate natural language therapy recommendations and session narratives. The operations additionally comprise training a deep neural network using a training dataset comprising autism-specific behavioral data, and training comprises applying data augmentation transformations to expand the training dataset and iteratively retraining to reduce classification errors. The operations also comprise generating, using the trained deep neural network, personalized therapy content comprising adaptive learning modules, interactive games, and progress tracking visualizations. The operations further comprise transmitting the personalized therapy content to at least one client device for real-time therapy session delivery.

In accordance with yet another exemplary embodiment, an immersive therapy system is provided. The system comprises a head-mounted display device configured to present at least one of augmented reality content overlaid on a real-world environment or virtual reality content depicting a simulated environment. The system further comprises at least one sensor configured to capture client interaction data during a therapy session. The system additionally comprises at least one processor communicatively coupled to the head-mounted display device and the at least one sensor. The system also comprises at least one non-transitory computer-readable medium storing instructions that, when executed by the at least one processor, cause the system to render, on the head-mounted display device, a simulated real-world scenario selected from a plurality of life skills training scenarios including street crossing navigation, social interaction practice, retail transaction completion, or transportation facility navigation. The instructions further cause the system to receive, from the at least one sensor, real-time client interaction data comprising at least one of gaze tracking data, gesture recognition data, verbal response data, or physiological response data. The instructions additionally cause the system to analyze the real-time client interaction data using a trained machine learning model to determine client engagement level and task performance metrics. The instructions also cause the system to dynamically modify the simulated real-world scenario based on the determined client engagement level and task performance metrics to maintain optimal challenge level for skill acquisition.

Further exemplary embodiments provide a caregiver training platform comprising a computing device configured to present interactive training modules for Applied Behavior Analysis techniques. The training modules are generated by a large language model and customized based on client-specific therapy goals and caregiver learning progress metrics.

Additional exemplary embodiments provide methods and systems for expanding access to Applied Behavior Analysis therapy services through telehealth delivery platforms that integrate artificial intelligence-driven session planning, real-time behavioral data collection, and outcome tracking to achieve therapeutic outcomes comparable to or exceeding traditional in-person therapy delivery while reducing required therapy hours.

BRIEF DESCRIPTION OF THE DRAWINGS

The following description and drawings set forth certain illustrative implementations in detail, which are indicative of several exemplary ways in which the various principles described herein may be carried out. The illustrative examples, however, are not exhaustive of the many possible embodiments. Other objects, advantages, and novel features will become apparent from the following detailed description when considered in conjunction with the drawings, in which:

FIG. 1 shows an exemplary deep neural network to analyze client data and generate tailored sessions, assessments, and gamified content.

FIG. 2 shows an exemplary block diagram of a system architecture for artificial intelligence-driven therapy delivery according to an exemplary embodiment.

FIG. 3 shows how an exemplary large language model learns and trains itself using model prompts, user input, and multi-modal training data to support session planning, assessments, and real-time adjustments.

FIG. 5 shows exemplary curriculum that may be tailored to individual therapy goals and delivered through various formats, including interactive games, multimedia presentations, and AR/VR technology of FIG. 4.

FIG. 6 shows an exemplary block diagram of a telehealth platform for delivering Applied Behavior Analysis therapy services according to an exemplary embodiment.

FIG. 7 shows an exemplary data flow diagram depicting the integration of multiple data sources for personalized therapy session generation according to an exemplary embodiment.

DETAILED DESCRIPTION

Figure 4:
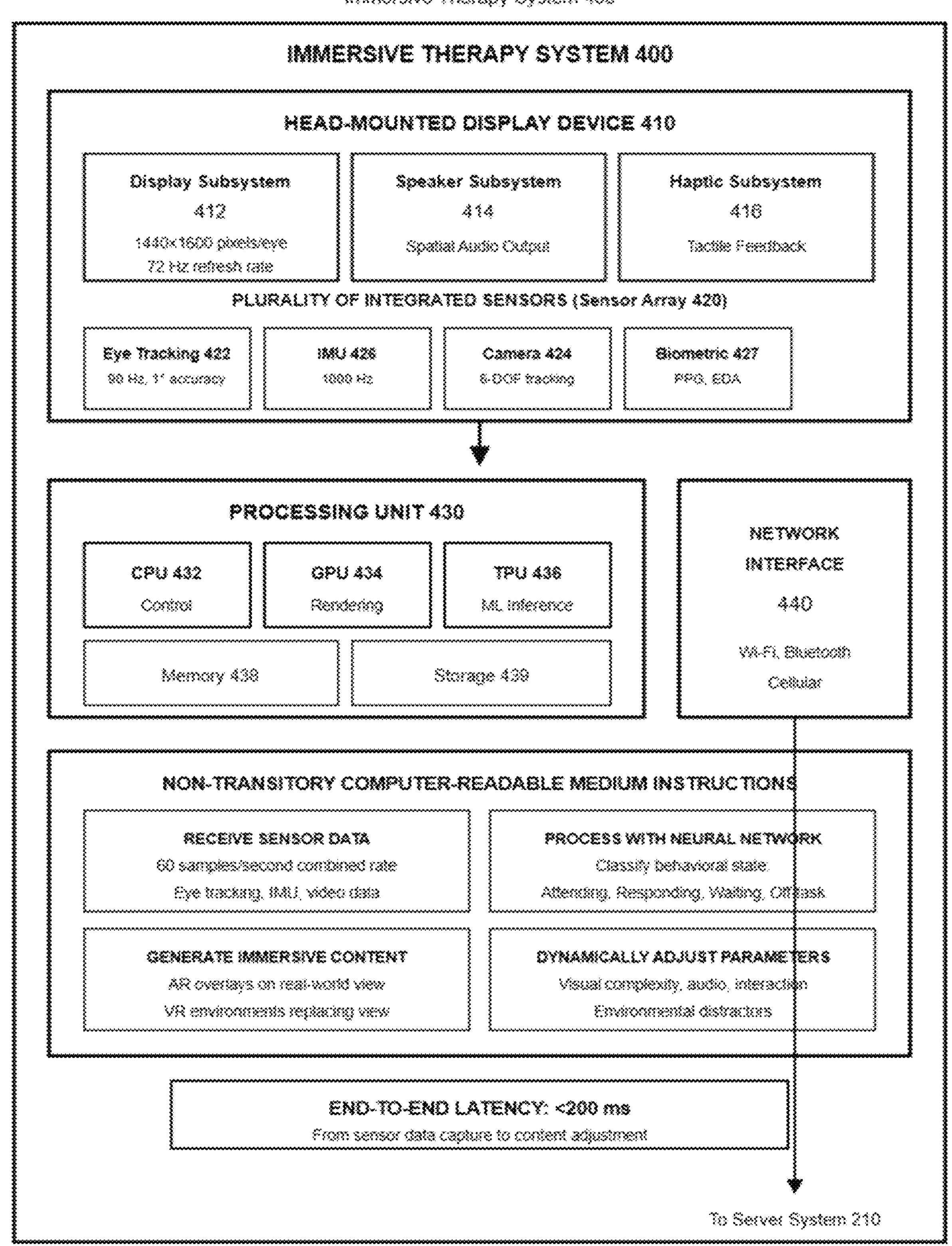
FIG. 4 shows a client with exemplary Augmented Reality (AR) glasses and/or Virtual Reality (VR) goggles for immersive and interactive therapy scenarios, including real-world skill simulations and training exercises.

Existing computer systems for therapy delivery suffer from several technical deficiencies. First, conventional systems lack the computational architecture necessary to process multimodal sensor data streams in real time while simultaneously executing machine learning inference operations. The latency introduced by sequential processing of sensor data, behavioral analysis, and content adaptation exceeds acceptable thresholds for interactive therapy applications, resulting in delayed system responses that disrupt therapeutic engagement. Second, conventional neural network architectures trained on general datasets fail to accurately classify autism-specific behavioral patterns due to the high variability and subtlety of such patterns, resulting in classification error rates that render automated analysis unreliable. Third, conventional virtual and augmented reality systems lack integration with behavioral analysis systems, requiring manual clinician intervention to adjust content parameters, which introduces delays that exceed the time window required for effective behavioral reinforcement.

The exemplary embodiments described herein provide technical solutions to these technical problems. The disclosed system architecture implements processing pipelines that execute sensor data ingestion, neural network inference, and content rendering operations across specialized processor units (GPUs, TPUs, NPUs), reducing end-to-end latency compared to conventional sequential architectures. The disclosed training methodology implements an iterative error correction algorithm that specifically targets autism-specific behavioral pattern classification, reducing classification error rates through systematic identification and incorporation of misclassified instances into refined training datasets. The disclosed immersive therapy system implements direct hardware integration between sensor subsystems and content rendering engines enabling content adaptation within the time window required for effective behavioral intervention.

Technical Problem and Solution

The technical problems addressed by the exemplary embodiments are rooted in the architecture of computing systems rather than in the abstract concept of therapy itself. Conventional computing architectures for sensor-based interactive systems employ sequential processing in which sensor data acquisition, analysis, decision-making, and content rendering occur in serial fashion on general-purpose processors. This sequential architecture creates a computational bottleneck: each processing stage must complete before the next begins, and the cumulative latency of all stages exceeds the biologically-determined time window within which stimulus-response associations can be formed. Specifically, behavioral science literature establishes that reinforcement contingencies must occur within 200 milliseconds of the target behavior to establish effective conditioning. Sequential processing architectures on conventional hardware exhibit end-to-end latencies exceeding 500 milliseconds—more than twice the acceptable threshold—rendering them technically incapable of supporting real-time behavioral intervention applications regardless of the sophistication of the underlying algorithms.

The exemplary embodiments provide a technical solution to this computational bottleneck through a parallel processing pipeline architecture that decouples processing stages and executes them concurrently on heterogeneous processor resources. The technical improvement achieved by this architecture is measurable and concrete: end-to-end latency is reduced from greater than 500 milliseconds to less than 200 milliseconds, representing at least a 60% reduction in processing time. This improvement is achieved through specific technical means: allocating the sensor data ingestion stage to dedicated CPU cores optimized for I/O operations; allocating the neural network inference stage to GPU or TPU resources optimized for the matrix multiplication operations fundamental to neural network computation; allocating the rule-based adaptation stage to CPU resources optimized for conditional logic execution; and allocating the rendering stage to GPU resources optimized for graphics generation. The shared memory buffer architecture enables these stages to operate asynchronously, with each stage reading from and writing to dedicated memory regions without blocking other stages.

A second technical problem addressed by the exemplary embodiments concerns the accuracy of neural network classification when applied to autism-specific behavioral data. Neural networks trained on general behavioral datasets exhibit classification error rates exceeding 30% when applied to autism-specific behavioral patterns due to the high intra-class variability and subtle distinguishing features characteristic of this population. This technical deficiency renders such general-purpose models unsuitable for automated behavioral analysis in therapeutic contexts, where misclassification can lead to inappropriate intervention timing and ineffective treatment. The technical cause of this deficiency lies in the distribution mismatch between general training data and the specific patterns present in the target population, resulting in learned feature representations that fail to capture the relevant discriminative information.

The exemplary embodiments provide a technical solution through an iterative training algorithm that systematically identifies and corrects classification errors. The algorithm operates by evaluating model performance on a validation dataset, identifying instances that are misclassified, analyzing the feature representations of misclassified instances to identify systematic error patterns, constructing a refined training dataset that oversamples difficult cases, and retraining the model on the refined dataset. This iterative process continues until the classification error rate falls below a predetermined threshold (10% in exemplary embodiments). The technical improvement is concrete and measurable: classification error rates are reduced from initial values exceeding 30% to final values below 8%, representing a reduction of more than 70% in classification errors. This improvement enables reliable automated behavioral analysis that was not achievable with prior approaches.

A third technical problem addressed by the exemplary embodiments concerns the integration of sensor subsystems with content rendering systems in immersive display devices. Conventional virtual reality and augmented reality systems maintain separation between sensor processing pipelines and rendering pipelines, requiring inter-process communication through operating system facilities that introduce latency on the order of tens of milliseconds per communication event. When multiple sensor modalities must be processed and multiple content parameters must be adjusted, the cumulative communication overhead exceeds acceptable latency thresholds. The technical cause is the software architecture of conventional systems, which treats sensing and rendering as separate concerns connected through loosely-coupled interfaces.

The exemplary embodiments provide a technical solution through direct hardware integration of sensor subsystems and rendering engines via shared memory structures accessible to both subsystems without operating system intervention. Specifically, sensor data is written directly to memory-mapped buffers that are simultaneously readable by the rendering engine, eliminating the serialization and deserialization overhead of conventional inter-process communication. The rendering engine maintains pre-computed content variations for different adaptation states, enabling instantaneous switching between content configurations rather than runtime content generation. This architecture reduces adaptation latency from sensor event to rendered content change to less than 200 milliseconds total, enabling content modifications to occur within the time window required for effective behavioral reinforcement.

The parallel processing pipeline architecture achieves its latency reduction through specific hardware and software implementation choices. The ingestion stage executes on one or more CPU cores configured with elevated thread priority and CPU affinity to minimize context switching overhead. The ingestion stage maintains a ring buffer with capacity for at least 2 seconds of sensor data (approximately 180 samples at 90 Hz for eye tracking data, 2000 samples at 1000 Hz for IMU data, and 60 frames at 30 Hz for video data), enabling the analysis stage to process data batches without blocking ingestion of new data. The analysis stage executes neural network inference using batched processing on GPU resources, with batch sizes dynamically adjusted based on available GPU memory and current processing load to maximize throughput while maintaining latency constraints. In exemplary embodiments, batch sizes of 4 to 8 samples provide optimal throughput-latency tradeoffs for the neural network architectures described herein. The adaptation stage implements a state machine with precomputed transition tables that map combinations of behavioral state classifications and engagement levels to content parameter adjustments, enabling O(1) lookup time for adaptation decisions. The rendering stage maintains a pool of pre-allocated graphics resources for each content variation, enabling parameter changes to be applied through resource pointer updates rather than resource regeneration.

The neural network architecture achieves its classification accuracy through specific design choices tailored to the characteristics of multimodal behavioral data. The parallel convolutional branches in the feature extraction module employ different kernel sizes and strides optimized for each modality: 7×7 kernels with stride 2 for video data to capture spatial patterns at multiple scales; 1D kernels of length 64 with stride 4 for audio data to capture temporal patterns in waveforms; graph convolutions over the skeletal joint adjacency matrix for motion data to capture anatomically-meaningful movement patterns; and fully-connected layers for physiological data to capture correlations between different physiological channels. The bidirectional LSTM in the temporal processing module processes sequences of 30 time steps (corresponding to 1 second of data at 30 Hz) in both forward and backward directions, enabling the model to capture temporal dependencies that span the entire observation window. The use of bidirectional processing provides the model with future context that improves classification accuracy for behavioral states that are characterized by temporal trajectories rather than instantaneous features.

The dynamic difficulty adjustment algorithm achieves its adaptation responsiveness through specific parameter choices that balance stability with responsiveness. The sliding window size of 10 trials provides sufficient statistical power to detect genuine performance trends while remaining responsive to rapid changes in client state. The success rate thresholds of 0.80 for difficulty increase and 0.60 for difficulty decrease create a hysteresis band that prevents oscillation around the target success rate of 0.70 to 0.80. The cooldown period of 3 trials following each adjustment prevents rapid successive adjustments that could create confusing task sequences for clients. These parameters are configurable on a per-client basis to accommodate individual differences in learning rates and tolerance for challenge variability.

The engagement level calculation achieves its multi-factor sensitivity through weighted combination of heterogeneous sensor inputs with sensor-specific normalization. The gaze engagement component normalizes fixation duration relative to the measurement window duration, producing values that are comparable across different task types with different expected viewing patterns. The response engagement component normalizes response latency relative to client-specific baseline latencies, producing values that account for individual differences in processing speed that are unrelated to engagement. The interaction frequency component normalizes interaction count relative to expected interaction rates for the specific task type, producing values that account for structural differences between tasks that require different interaction patterns. The physiological engagement component normalizes heart rate variability and galvanic skin response relative to calibration baselines established for each client, producing values that account for individual differences in physiological reactivity. The weighted combination of these normalized components produces an engagement score that is interpretable and actionable regardless of the specific sensor configuration or task type in use.

Definitions

As used herein, the following terms have the specified meanings unless context clearly indicates otherwise. These definitions apply throughout this specification and the appended claims.

The term "client" refers to an individual receiving Applied Behavior Analysis therapy or developmental support services, and may be used interchangeably with "patient" or "learner" depending on context. The term "caregiver" refers to any individual providing care or support to a client, including but not limited to parents, guardians, family members, teachers, aides, or professional care providers. The term "clinician" refers to a Board Certified Behavior Analyst (BCBA), Registered Behavior Technician (RBT), or other qualified professional delivering or supervising Applied Behavior Analysis therapy services.

The term "real time" or "real-time" refers to processing or response times that are sufficiently fast to enable interactive use. In the context of behavioral reinforcement applications, real-time refers to latencies of less than 200 milliseconds, which falls within the time window established in behavioral science literature as necessary for effective reinforcement contingency. In the context of content adaptation, real-time refers to modifications applied within 200 milliseconds of detecting a change in client engagement or performance metrics.

The term "dynamically" refers to operations performed during runtime or during an active session based on data collected during that runtime or session, as opposed to static or pre-configured operations determined prior to session initiation.

The term "engagement level" refers to a quantitative metric computed from one or more sensor inputs that indicates the degree to which a client is actively attending to and interacting with presented therapy content. Engagement level is computed as a normalized value between 0.0 and 1.0 indicating the degree of client engagement, incorporating weighted contributions from factors such as gaze fixation duration, response latency, interaction frequency, and physiological arousal indicators. An engagement level of at least 0.7 indicates high engagement; an engagement level of at least 0.4 and less than 0.7 indicates moderate engagement; an engagement level of at least 0.2 and less than 0.4 indicates low engagement; and an engagement level of less than 0.2 indicates disengagement.

The term "optimal challenge level" refers to a difficulty setting for therapy content that maximizes skill acquisition by presenting tasks that are achievable but require effort. Optimal challenge level is determined algorithmically based on recent task performance history, with difficulty adjusted to maintain task success rates within a target range of 0.70 to 0.80. This range corresponds to the zone of proximal development concept in educational psychology and the 70-80% success rate target established in Applied Behavior Analysis literature for promoting skill acquisition while maintaining client motivation.

The term "task performance metrics" refers to quantitative measurements of client performance on therapy tasks, including but not limited to: task completion rate (percentage of tasks successfully completed), response accuracy (percentage of correct responses), response latency (time elapsed between stimulus presentation and client response, measured in milliseconds), prompt level required (level of assistance required on a graduated prompt hierarchy from 0 for independent to 5 for full physical prompt), and generalization score (performance on novel variations of previously mastered tasks). For example, if a client completes 8 of 10 tasks correctly with an average response time of 1500 milliseconds and an average prompt level of 1.2, their metrics would be: task completion rate=80%, response latency=1500 ms, and mean prompt level=1.2.

The term "difficulty level" refers to a scalar value in the range of 1 to 10 representing the complexity of therapy content presented to a client, where 1 represents minimum difficulty and 10 represents maximum difficulty. Difficulty level 1 presents simple two-choice discrimination tasks with unlimited response time. Difficulty level 10 presents complex multi-step tasks with strict time limits and multiple distractors. Intermediate difficulty levels represent graduated steps between these extremes.

The term "prompt level" or "prompt intensity" refers to a scalar value in the range of 0 to 5 representing the amount of assistance provided to a client during a therapy task. A prompt level of 0 indicates independent performance with no assistance. A prompt level of 1 indicates a gestural prompt. A prompt level of 2 indicates a verbal prompt. A prompt level of 3 indicates a model prompt. A prompt level of 4 indicates a partial physical prompt. A prompt level of 5 indicates a full physical prompt.

The term "success rate" refers to the ratio of successful trials to total trials over a defined measurement period, expressed as a decimal value between 0.0 and 1.0. A success rate of 0.80 indicates that 80% of trials were completed successfully.

The term "sliding window" refers to a first-in-first-out data buffer that stores a fixed number of the most recent trial outcomes. When a new trial outcome is added and the buffer is full, the oldest trial outcome is removed.

The term "parallel processing pipeline" refers to a computing architecture in which multiple processing stages execute concurrently on dedicated processor resources, with data passed between stages via shared memory buffers or queues. Each stage operates independently and asynchronously from other stages, enabling continuous data flow and reduced end-to-end latency compared to sequential processing architectures.

The term "end-to-end latency" refers to the total time elapsed from initial data capture by a sensor to completion of a responsive action, measured in milliseconds. In the context of adaptive therapy systems, end-to-end latency is measured from receipt of client performance data to output of adjusted interactive content.

The term "behavioral state classification" refers to the categorization of observed client behavior into one of a predefined set of behavioral categories. Behavioral state categories include attending (client is focused on therapy content), responding (client is actively engaging with a task), waiting (client is paused between tasks), off-task (client attention is directed away from therapy content), self-stimulatory behavior (client is engaged in repetitive movements), and distressed (client exhibits signs of emotional dysregulation).

The term "multimodal sensor data" refers to data collected simultaneously from two or more different types of sensors, including but not limited to video cameras, audio microphones, eye tracking sensors, inertial measurement units, depth sensors, and physiological sensors such as photoplethysmography sensors and galvanic skin response sensors.

The term "confidence score" refers to a numerical value between 0.0 and 1.0 representing the degree of certainty associated with a classification or prediction generated by a machine learning model. A confidence score of 1.0 indicates complete certainty, while a confidence score of 0.0 indicates no certainty.

The term "reinforcement schedule" refers to the pattern or timing of reward delivery following correct client responses. Common reinforcement schedules include fixed ratio schedules (reinforcement after a fixed number of correct responses), variable ratio schedules (reinforcement after a variable number of correct responses averaging a specified value), fixed interval schedules (reinforcement after a fixed time period following a correct response), and variable interval schedules (reinforcement after a variable time period averaging a specified duration).

The term "environmental complexity" refers to the number and intensity of visual, auditory, and interactive elements present in a therapy environment. Higher environmental complexity includes more rendered objects, more detailed textures, more varied lighting, more audio sources, and more potential distractors.

The term "autism-specific behavioral data" refers to behavioral data collected from individuals diagnosed with autism spectrum disorder, annotated with clinician-verified labels indicating behavioral states, engagement levels, and therapy responses characteristic of the autism population.

Overview of Exemplary Embodiments

The exemplary embodiments described herein solve challenges in access to care, service delivery, engagement, and measurable outcomes for virtual Applied Behavior Analysis (ABA) therapy and caregiver training. The system features a unique intake process, including trial sessions to assess client (or "patient") eligibility for virtual services and whether adding Augmented Reality (AR) and Virtual Reality (VR) to the virtual therapy is a good fit. This approach facilitates early access to care, improves long-term outcomes, and reduces the duration of care episodes.

Unlike existing virtual methods that lack adaptability, engagement, and effectiveness, the exemplary embodiments herein provide a dynamic, data-driven approach tailored to individual client needs and deliver measurable progress. Therapy sessions are customized using real-time AI-driven algorithms to adjust content based on client behavior and performance data. Engagement is enhanced through gamification, interactive learning tools, and multimedia content, including but not limited to virtual reality environments. Virtual reality simulations replicate real-world scenarios, such as crossing a busy street, which cannot be safely practiced in person. Real-time data collection from VR and other session formats improves therapeutic outcomes by analyzing client performance, generating actionable insights, and predicting future needs. The system also expands access to ABA therapy for clients in underserved or remote areas, ensuring consistent care and measurable outcomes.

The exemplary approaches combine proven ABA methodologies with innovative technologies, such as AI, VR, and gamification to enhance client outcomes. The system delivers personalized, adaptive therapy plans, interactive presentations, and engaging content tailored for both clients and caregivers. Over 18 months, studies involving 1,200 clients showed that virtual clients required 33% fewer weekly treatment hours while achieving equivalent or improved gains compared to in-person therapy. These results highlight the system's ability to optimize therapy delivery, reduce required hours, and maintain or improve outcomes, offering scalability and accessibility that distinguish it from existing methods.

Beyond VR, the system uses AI to generate tailored session recommendations and dynamically create therapy content, including adaptive learning modules, interactive games, and personalized training exercises. AI enables fully customized therapy sessions for client progress and engagement. Augmented reality (AR) glasses guide clients visually through next steps and actions during therapy. Holographic virtual clinicians enhance immersion and accessibility, providing an innovative layer to therapy delivery. Eye-tracking technology analyzes client engagement and performance in virtual environments, refining content delivery. Together, these technologies support a comprehensive and adaptable therapy platform that maximizes client outcomes and caregiver involvement.

Deep Neural Network for Client Data Analysis (FIG. 1)

Referring now to FIG. 1, an exemplary deep neural network is depicted for analyzing client data and generating tailored sessions, adaptive training modules, and interactive learning content. The deep neural network comprises multiple layers of interconnected nodes that process input data through successive transformations to produce output classifications and recommendations.

The deep neural network of FIG. 1 receives client-specific input data including behavioral assessment scores, historical therapy session outcomes, caregiver-reported observations, and skill acquisition metrics. The input data is processed through an input layer that normalizes and formats the data for neural network processing. The normalized data passes through multiple hidden layers, each comprising nodes that compute weighted sums of inputs from the previous layer and apply nonlinear activation functions such as Rectified Linear Unit (ReLU) or sigmoid functions. The hidden layers extract increasingly abstract features from the input data, enabling the network to identify complex patterns in client behavior and therapy responses.

The output layer of the deep neural network produces therapy session recommendations including suggested therapy targets, difficulty levels, reinforcement schedules, and content selections. The network is trained using supervised learning on labeled datasets of client data and therapy outcomes, with backpropagation used to adjust network weights based on prediction errors. The trained network enables real-time inference to generate personalized therapy plans based on incoming client data.

With continued reference to FIG. 1, additional detail regarding the neural network architecture 100 is provided for behavioral pattern classification. The neural network architecture 100 provides detailed specifications for the deep neural network introduced in FIG. 1, comprising an input layer 110, a feature extraction module 120, a temporal processing module 130, a classification module 140, and an output layer 150.

The input layer 110 receives multimodal sensor data comprising video frame data, audio waveform data, motion tracking data, and physiological sensor data. Video frame data is represented as tensors of dimensions H×W×C, where H is frame height in pixels (typically 480 or 720), W is frame width in pixels (typically 684 or 1280), and C is the number of color channels (typically 3 for RGB). Audio waveform data is represented as one-dimensional tensors of length L, where L corresponds to the number of audio samples in a processing window (typically 16,000 samples for one second of 16 kHz audio). Motion tracking data is represented as tensors of dimensions T×J×3, where T is the number of time steps in a processing window (typically 30 for one second at 30 Hz), J is the number of tracked joints (typically 25 for full body tracking), and 3 represents x, y, z coordinates. Physiological sensor data is represented as tensors of dimensions T×P, where T is the number of time steps and P is the number of physiological channels (typically 4 for heart rate, galvanic skin response, skin temperature, and respiration rate).

The feature extraction module 120 comprises parallel convolutional neural network branches for processing each input modality. A video feature extraction branch 122 comprises a sequence of convolutional layers with the following architecture: a first convolutional layer with 64 filters of size 7×7 and stride 2, followed by batch normalization and ReLU activation; a max pooling layer with pool size 3×3 and stride 2; a second convolutional layer with 128 filters of size 3×3 and stride 1, followed by batch normalization and ReLU activation; a third convolutional layer with 256 filters of size 3×3 and stride 1, followed by batch normalization and ReLU activation; and a global average pooling layer producing a 256-dimensional feature vector. An audio feature extraction branch 124 comprises a one-dimensional convolutional architecture with similar layer progression producing a 128-dimensional feature vector. A motion feature extraction branch 126 comprises a graph convolutional network operating on the skeletal joint structure producing a 128-dimensional feature vector. A physiological feature extraction branch 128 comprises fully connected layers producing a 64-dimensional feature vector.

The temporal processing module 130 concatenates feature vectors from the feature extraction module 120 branches to produce a combined feature vector and processes the concatenated features through a bidirectional Long Short-Term Memory (LSTM) network. The LSTM network comprises two LSTM layers, each with 256 hidden units, processing input sequences in both forward and backward directions. The output of the temporal processing module 130 is a 512-dimensional representation capturing temporal dynamics across the multimodal input streams.

The classification module 140 comprises a series of fully connected layers that transform the temporal representation into classification outputs. A first fully connected layer transforms the 512-dimensional input to 256 dimensions with ReLU activation and dropout with probability 0.5. A second fully connected layer transforms the 256-dimensional input to 128 dimensions with ReLU activation and dropout with probability 0.3. A third fully connected layer transforms the 128-dimensional input to the number of output classes.

The output layer 150 applies softmax activation for classification tasks or sigmoid activation for multi-label tasks. For engagement level prediction, the output layer 150 produces a single scalar value between 0.0 and 1.0 using sigmoid activation. For behavioral state classification, the output layer 150 produces probability distributions over predefined behavioral categories including attending, responding, waiting, off-task, self-stimulatory behavior, and distressed, using softmax activation.

System Architecture (FIG. 2)

Referring now to FIG. 2, an exemplary system architecture 200 for artificial intelligence-driven therapy delivery is depicted according to an exemplary embodiment. The system architecture 200 comprises a server computing system 210, one or more client devices 220, one or more clinician devices 230, one or more caregiver devices 240, and a network 250 communicatively coupling the components.

The server computing system 210 comprises at least one processor 212, at least one memory 214, and at least one non-transitory computer-readable storage medium 216. The at least one processor 212 may comprise one or more central processing units (CPUs), one or more graphics processing units (GPUs), one or more tensor processing units (TPUs), one or more neural processing units (NPUs), or combinations thereof. In exemplary embodiments, the at least one processor 212 is configured to execute machine learning models including deep neural networks and large language models as described herein.

The server computing system 210 further comprises a therapy engine module 218 configured to process client data and generate personalized therapy session plans, a content generation module 219 configured to create interactive learning modules and therapy content, a data analytics module 217 configured to analyze therapy outcomes and generate progress reports, and an application programming interface (API) 215 configured to enable communication with client devices 220, clinician devices 230, and caregiver devices 240. In exemplary embodiments, the server computing system 210 operates as a unified digital platform that centralizes therapy delivery, content generation, data analytics, and quality evaluation across multiple service modalities. The platform maintains a single system of record for client data, therapy content, session analytics, and performance monitoring, while supporting role-specific interfaces for clinicians, caregivers, and clients. This enables scalable deployment of artificial intelligence-driven therapy, telehealth services, and caregiver training within a single integrated system.

The client devices 220 may comprise tablet computers, smartphones, desktop computers, laptop computers, head-mounted display devices, or other computing devices configured to present therapy content to clients. The clinician devices 230 may comprise computing devices used by therapists to monitor sessions, review client progress, and adjust therapy parameters. The caregiver devices 240 may comprise computing devices used by parents, guardians, or other caregivers to access training content, view client progress, and communicate with clinicians.

The network 250 comprises one or more communication networks including the Internet, local area networks (LANs), wireless networks, cellular networks, or combinations thereof. The network 250 enables bidirectional communication between the server computing system 210 and the various client, clinician, and caregiver devices.

With continued reference to FIG. 2, the system architecture 200 includes a parallel processing pipeline 260. The parallel processing pipeline 260 addresses the technical problem of processing latency in real-time behavioral analysis systems by implementing concurrent execution paths for different processing stages. The parallel processing pipeline 260 comprises a sensor data ingestion stage 262, a behavioral analysis stage 264, a content adaptation stage 266, and a rendering stage 268, each executing on dedicated processor resources.

The sensor data ingestion stage 262 executes on a dedicated CPU core or set of cores and is responsible for receiving raw sensor data from client devices, performing initial signal processing including noise filtering and normalization, and writing processed sensor data to a shared memory buffer 270. The sensor data ingestion stage 262 operates continuously at a rate of at least 60 samples per second for motion tracking data and at least 30 samples per second for video data.

The behavioral analysis stage 264 executes on GPU or TPU resources and is responsible for executing neural network inference operations on sensor data read from the shared memory buffer 270. The behavioral analysis stage 264 implements the trained behavioral classification neural network described herein to generate engagement level scores, behavioral state classifications, and performance metrics. The behavioral analysis stage 264 writes analysis results to an analysis output buffer 272. The behavioral analysis stage 264 operates asynchronously from the sensor data ingestion stage 262, processing sensor data batches as they become available while the sensor data ingestion stage 262 continues to collect new data.

The content adaptation stage 266 executes on CPU resources and is responsible for reading analysis results from the analysis output buffer 272 and determining appropriate content modifications based on the dynamic difficulty adjustment algorithm described herein. The content adaptation stage 266 generates content modification commands that specify parameter changes such as difficulty level, prompt intensity, reinforcement schedule, or environmental complexity. The content adaptation stage 266 writes content modification commands to a rendering command queue 274.

The rendering stage 268 executes on GPU resources and is responsible for reading content modification commands from the rendering command queue 274 and updating the visual, auditory, and haptic content presented to the client via the display device. The rendering stage 268 maintains a target frame rate of at least 72 frames per second for virtual reality content and at least 60 frames per second for augmented reality content to prevent motion sickness and maintain immersion.

The shared memory buffer 270, analysis output buffer 272, and rendering command queue 274 enable concurrent read and write access, minimizing pipeline stalls and maintaining consistent throughput. The end-to-end latency from sensor data capture to rendered content update is maintained at less than 200 milliseconds, representing a reduction of at least 60% compared to conventional sequential processing architectures that typically exhibit latencies exceeding 500 milliseconds.

Large Language Model Integration (FIG. 3)

Referring now to FIG. 3, an exemplary large language model (LLM) is depicted, showing a user prompt, the LLM itself, training data, and a model output. A user prompt in a large language model (LLM) is a text input designed to guide the LLM in generating a specific output. The prompt specifies the desired type, style, and tone of the LLM's output. The quality of the model output generated by an LLM is heavily influenced by the quality of the prompt. A well-crafted prompt enables the LLM to generate output that is relevant, accurate, and creative.

A large language model (LLM) is an artificial intelligence (AI) system trained on extensive text datasets. These datasets include text from books, articles, websites, and other sources. LLMs learn patterns and structures within text, enabling them to generate new content, translate languages, create interactive learning materials, and answer questions informatively.

In exemplary embodiments, the large language model is utilized to generate natural language content for therapy applications including: session narrative generation, the LLM transforms structured session data into readable narrative summaries for clinical documentation; interactive dialogue generation, the LLM generates contextually appropriate verbal prompts, praise statements, and corrective feedback delivered by virtual clinician avatars; caregiver instruction generation, the LLM generates personalized written instructions for caregivers based on current therapy targets and strategies; and social narrative generation, the LLM generates social stories and scripts tailored to individual client situations and comprehension levels.

The large language model is fine-tuned on domain-specific training data comprising clinical documentation from Applied Behavior Analysis therapy, including session notes, assessment reports, treatment plans, and professional literature. Fine-tuning adapts the general language model to generate text consistent with ABA terminology, evidence-based practices, and clinical documentation standards. Fine-tuning is performed using supervised learning on input-output pairs of clinical scenarios and appropriate text responses, with human clinician review of generated outputs to ensure accuracy and appropriateness.

With continued reference to FIG. 3, an exemplary method 300 for training and deploying a neural network for autism intervention applications is described. The method 300 begins at block 302 with data collection, in which autism-specific behavioral data is collected from clinical sources including therapy session recordings, clinician annotations, and standardized assessment results.

At block 304, data preprocessing is performed, the collected data is cleaned, normalized, and formatted for neural network training. Preprocessing includes removing corrupted or incomplete records, normalizing numerical values to standard ranges, and converting categorical variables to numerical representations.

At block 306, data augmentation is applied to expand the training dataset. Data augmentation techniques include geometric transformations for video data, temporal modifications for time-series data, and text augmentation for natural language data. The augmented dataset provides greater variability for model training and improves generalization performance.

At block 308, the neural network architecture is defined, specifying the number and types of layers, activation functions, and connections between layers. The architecture is selected based on the specific task requirements, with convolutional layers for visual data processing, recurrent layers for temporal sequence processing, and fully connected layers for classification.

At block 310, the neural network is trained using the augmented training dataset. Training proceeds iteratively, with model weights adjusted using backpropagation to minimize the loss function. Training continues until convergence criteria are met or a maximum number of epochs is reached.

At block 312, the trained model is evaluated on a held-out validation dataset to assess performance metrics including accuracy, precision, recall, and F1-score. If performance metrics do not meet target thresholds, the method returns to block 306 or block 308 for dataset refinement or architecture modification.

At block 314, the validated model is deployed to production systems, where it is integrated with the therapy delivery platform for real-time inference. Deployment includes model optimization for inference speed, integration with data pipelines, and configuration of monitoring systems.

At block 316, ongoing monitoring tracks model performance in production, with alerts generated if performance degrades below acceptable thresholds. Periodic retraining is scheduled to incorporate new data and maintain model accuracy over time.

With continued reference to FIG. 3, an iterative training algorithm 350 with error correction is described. The iterative training algorithm 350 addresses the technical problem of high classification error rates in autism-specific behavioral pattern recognition by systematically identifying and correcting classification errors through multiple training iterations.

At block 352, an initial training dataset D0 is assembled comprising autism-specific behavioral data collected from clinical sources. The initial training dataset D0 comprises labeled video recordings of therapy sessions, clinician annotations of behavioral states, standardized assessment results, and session outcome data. In exemplary embodiments, the initial training dataset D0 comprises at least 10,000 labeled examples across at least 600 unique clients to provide sufficient variability for generalization.

At block 354, data augmentation transformations are applied to the initial training dataset D0 to generate an expanded training dataset D0-aug. Data augmentation transformations for video data comprise random horizontal flipping with probability 0.5, random rotation within plus or minus 15 degrees, random scaling between 0.9 and 1.1, random brightness adjustment within plus or minus 20%, random contrast adjustment within plus or minus 20%, and temporal jittering by randomly dropping or duplicating frames with probability 0.1 per frame. Data augmentation transformations for audio data comprise random time stretching between 0.9 and 1.1, random pitch shifting within plus or minus 2 semitones, random noise injection with signal-to-noise ratio between 20 dB and 40 dB, and random volume adjustment within plus or minus 10 dB. Data augmentation transformations increase the effective training dataset size by a factor of 5 to 10.

At block 356, the neural network model is initialized with random weights drawn from a Xavier uniform distribution and trained on the expanded training dataset D0-aug using the Adam optimizer with initial learning rate 0.001, beta1 0.9, beta2 0.999, and epsilon 1e−8. Training proceeds for a maximum of 200 epochs with early stopping based on validation loss with patience of 10 epochs. The loss function comprises categorical cross-entropy for classification outputs and mean squared error for regression outputs, with optional regularization terms including L2 weight decay with coefficient 0.0001.

At block 358, the trained model is evaluated on a held-out validation dataset Dval comprising at least 20% of the original data not used in training. Evaluation metrics comprise accuracy, precision, recall, F1-score for each class, and area under the receiver operating characteristic curve (AUC-ROC). Classification errors are identified as instances where the model prediction differs from the ground truth label.

At block 360, a determination is made whether the classification error rate on the validation dataset exceeds a threshold. In exemplary embodiments, the error rate threshold is 10%. If the error rate exceeds the threshold, processing proceeds to block 362. If the error rate is at or below the threshold, training is complete and the model is deployed at block 368.

At block 362, misclassified instances from the validation dataset are collected and analyzed to identify patterns of errors. Error analysis comprises computing confusion matrices to identify commonly confused class pairs, examining feature representations of misclassified instances using dimensionality reduction techniques such as t-SNE or UMAP, and clustering misclassified instances to identify systematic error patterns.

At block 364, a refined training dataset Di+1 is constructed by combining the previous training dataset Di with the misclassified instances, optionally with increased sampling weight for misclassified instances. In exemplary embodiments, misclassified instances are oversampled by a factor of 3 to 5 to emphasize learning from errors. Additional targeted data collection may be performed to gather more examples similar to misclassified instances.

At block 366, the neural network model is retrained on the refined training dataset Di+1. Retraining may proceed from the previously trained weights (fine-tuning) or from reinitialized weights depending on the magnitude of dataset changes. In exemplary embodiments, fine-tuning is used when the refined dataset comprises less than 20% new data, and full retraining is used otherwise. Processing then returns to block 356 for re-evaluation.

The iterative training algorithm 350 typically converges within 3 to 5 iterations, reducing classification error rates from initial values exceeding 30% to final values below 8%. This represents a technical improvement in classification accuracy that enables reliable automated behavioral analysis for therapeutic applications.

Augmented Reality and Virtual Reality Integration (FIG. 4)

Referring now to FIG. 4, a client is depicted using Augmented Reality (AR) glasses and/or Virtual Reality (VR) goggles during a therapy session. Augmented Reality (AR) glasses and Virtual Reality (VR) goggles integrate advanced technologies to create immersive, interactive experiences for therapy and training. Artificial Intelligence (AI), such as Large Language Models (LLMs) and Neural Networks, enhances the responsiveness and intelligence of these systems.

The AR glasses depicted in FIG. 4 enable overlay of digital guidance, instructions, and visual cues onto the client's real-world environment. This augmented display guides clients through therapy activities by highlighting objects, displaying step-by-step instructions, and providing visual feedback on task performance. The VR goggles depicted in FIG. 4 provide fully immersive virtual environments that simulate real-world scenarios for safe skill practice.

The client shown in FIG. 4 interacts with the AR/VR system through natural movements, gestures, and verbal responses. Sensors integrated into the headset track the client's head position, gaze direction, and hand movements to enable intuitive interaction with virtual content. The system adapts content presentation in real time based on the client's responses and engagement level.

With continued reference to FIG. 4, an immersive therapy system 400 incorporating augmented reality and virtual reality components is described. The immersive therapy system 400 comprises a head-mounted display (HMD) device 410, a sensor array 420, a processing unit 430, and a network interface 440.

The head-mounted display device 410 may comprise augmented reality glasses, virtual reality goggles, or a mixed reality headset. The head-mounted display device 410 comprises a display subsystem 412 having high-resolution micro-displays (1440×1600 pixels per eye at 72 Hz minimum) for rendering visuals to a user, a speaker subsystem 414 for audio output, and a haptic feedback subsystem 416 for tactile feedback. In augmented reality embodiments, the display is at least partially transparent to allow viewing of a real-world environment with digital content overlaid thereon. In virtual reality embodiments, the display provides a fully immersive view of a computer-generated environment. Display specifications include minimum resolution of 1440×1600 pixels per eye, minimum refresh rate of 72 Hz, and field of view of at least 90 degrees to provide adequate immersion for therapeutic applications.

The sensor array 420 comprises one or more sensors configured to capture data regarding a user, the user's environment, and user interactions with the system. The sensor array 420 comprises an eye tracking subsystem 422, a camera subsystem 424, an inertial measurement unit (IMU) subsystem 426, a depth sensing subsystem, a microphone subsystem, and a biometric sensor subsystem 427. Specifically, the sensor array 420 comprises inside-out tracking cameras for 6-degree-of-freedom head position tracking with suitable accuracy; depth sensors such as LiDAR, structured light sensors, or time-of-flight sensors for spatial mapping of the physical environment; inertial measurement units (IMUs) including 3-axis gyroscopes and 3-axis accelerometers for tracking head orientation and movement at sampling rates of at least 1000 Hz; eye tracking cameras operating at minimum 90 Hz with infrared illumination for determining gaze direction with accuracy of 1 degree or better and pupil dilation measurement; integrated or peripheral microphones for capturing voice input with noise cancellation capability; and optional biometric sensors including photoplethysmography (PPG) sensors for heart rate measurement and electrodermal activity (EDA) sensors for galvanic skin response measurement.

The processing unit 430 comprises a central processing unit (CPU) 432 for control operations, a graphics processing unit (GPU) 434 for rendering, a neural processing unit (NPU) or tensor processing unit (TPU) 436 for machine learning inference, memory 438, and storage 439. The processing unit 430 executes software for rendering virtual content, processing sensor data, and communicating with external systems. The processing unit 430 may be integrated within the head-mounted display device 410 or may comprise an external computing device communicatively coupled to the head-mounted display device 410 via wired or wireless connection.

The network interface 440 enables communication between the immersive therapy system 400 and the server computing system 210 described with reference to FIG. 2. The network interface 440 may comprise Wi-Fi, Bluetooth, cellular, or wired Ethernet connectivity.

Curriculum and Life Skills Training Content (FIG. 5)

Referring now to FIG. 5, exemplary curriculum content is depicted that may be delivered through AR glasses or VR goggles as shown in FIG. 4. Studies indicate that neural experiences in virtual and augmented environments closely match those in real-world settings. Exemplary curriculum provides essential life skills for individuals with autism or other developmental conditions. Examples include crossing a busy street, taking turns, navigating airports, grocery shopping, and learning pet care. The exemplary system supports supervised learning, where clinicians input guidance via electronic devices during sessions, enhancing both the learner's progress and AI's adaptation. Curriculum customization may correlate with client profiles and data to optimize outcomes.

The curriculum content library comprises a plurality of learning modules organized into skill domains. Each learning module is parameterized to enable difficulty adjustment and personalization. Skill domains and exemplary modules include: Safety Skills comprising street crossing (parameters: number of lanes, traffic density, signal types, distractor intensity), fire safety (parameters: alarm types, exit complexity, smoke presence), and stranger safety (parameters: scenario types, social pressure level, escape options); Daily Living Skills comprising meal preparation (parameters: recipe complexity, appliance types, timing requirements), personal hygiene (parameters: routine length, sensory factors, independence level), and household chores (parameters: task complexity, tool requirements, completion standards); Community Skills comprising grocery shopping (parameters: store layout complexity, item count, budget constraints, social interaction requirements), restaurant dining (parameters: menu complexity, ordering method, social expectations), and public transportation (parameters: route complexity, schedule adherence, transfer requirements); and Social Skills comprising greeting interactions (parameters: formality level, familiarity, cultural context), conversation maintenance (parameters: topic complexity, turn-taking requirements, nonverbal cue intensity), and conflict resolution (parameters: conflict severity, emotional intensity, resolution strategies).

With continued reference to FIG. 5, an exemplary method 500 for dynamically generating and adapting therapy content based on real-time client performance data is described.

At block 510, the method 500 receives client profile data including historical therapy outcomes, current skill levels, identified challenges, and therapy goals. The client profile data is retrieved from the database stored on the server computing system 210.

At block 520, the method 500 analyzes the client profile data using the trained neural network to identify appropriate starting parameters for therapy content. Analysis considers the client's demonstrated skill levels, sensory preferences, attention patterns, and reinforcement history.

At block 530, the method 500 generates initial therapy content with parameters selected based on the analysis. Content generation includes selecting appropriate scenarios, setting difficulty levels, configuring visual and auditory elements, and establishing reinforcement schedules.

At block 540, the method 500 presents the generated content to the client via the display device and monitors client responses through the sensor array. Real-time data collection captures response accuracy, response latency, engagement indicators, and behavioral state.

At block 550, the method 500 analyzes collected performance data to determine whether content adaptation is indicated. Adaptation triggers include sustained low engagement, error patterns indicating excessive difficulty, or consistent high performance indicating insufficient challenge.

At 560, if adaptation is indicated, the method 500 modifies content parameters according to the dynamic difficulty adjustment algorithm and returns to block 540 to continue presenting adapted content. If adaptation is not indicated, processing continues with current content parameters.

At block 570, when the session concludes, the method 500 generates session summary data and stores outcomes in the client profile for use in future sessions.

Telehealth Platform for ABA Therapy Services (FIG. 6)

Referring now to FIG. 6, an exemplary block diagram depicts a telehealth platform 600 for delivering Applied Behavior Analysis therapy services according to an exemplary embodiment. The telehealth platform 600 enables remote delivery of therapy services through videoconferencing combined with AI-assisted data collection and session management.

The telehealth platform 600 comprises a videoconferencing module 610 configured to establish real-time audiovisual communication between clinician devices and client devices with latency of less than 150 milliseconds suitable for real-time interaction. The videoconferencing module 610 supports features including screen sharing for stimulus presentation, remote annotation for clinician guidance, and recording for later review.

The telehealth platform 600 further comprises a session management module 620 configured to schedule therapy sessions, manage session state, and coordinate transitions between session activities. The session management module 620 maintains records of scheduled and completed sessions, tracks attendance, and generates reminders for upcoming sessions.

The telehealth platform 600 further comprises a data collection module 630 configured to automatically record trial data during therapy sessions. The data collection module 630 captures stimulus presentation events, client response events, response latencies, prompt levels delivered, and trial outcomes without requiring manual data entry by clinicians.

The telehealth platform 600 further comprises an AI therapy engine 640 that implements the trained neural network models to analyze session data, detect patterns, and generate recommendations. The AI therapy engine 640 identifies response biases, predicts learning trajectories, and suggests session modifications in real time.

The telehealth platform 600 further comprises a reporting module 650 configured to generate progress reports, acquisition curves, and clinical documentation. The reporting module 650 produces standardized reports suitable for insurance submissions, school districts, and clinical records. In exemplary embodiments, caregiver training and engagement functionality is delivered through a dedicated caregiver-facing application executed on caregiver devices. The application provides guided training modules, session summaries, home practice recommendations, and progress visualization derived from therapy session data. The caregiver-facing application communicates with the server computing system to receive personalized content and transmit caregiver interaction data for analysis, enabling continuous caregiver support and alignment with therapy goals outside of live sessions.

The telehealth platform 600 further comprises an integration module 660 configured to exchange data with external systems including electronic health records (EHR), practice management systems, and insurance billing systems using standard healthcare interoperability protocols including Health Level Seven (HL7) and Fast Healthcare Interoperability Resources (FHIR). In exemplary embodiments, the telehealth platform 600 further includes an automated quality evaluation subsystem configured to analyze recorded therapy session transcripts using artificial intelligence. The subsystem extracts conversational metrics including clarity, engagement, pacing, and responsiveness, and evaluates session performance against a configurable rubric defined by domain experts. Quantitative quality scores and automated coaching feedback are generated when performance deviates from predefined thresholds, enabling scalable quality assurance without manual session review. The configurable rubric comprises anchored scoring criteria, and the quality scores are generated independent of visual appearance data to focus evaluation on conversational and behavioral metrics.

With continued reference to FIG. 6, an exemplary method 680 for caregiver training and engagement tracking is described. The method 680 provides structured training to caregivers of individuals receiving ABA therapy, enabling caregivers to support skill generalization and maintenance outside of formal therapy sessions.

At block 681, the method 680 receives caregiver profile data including the caregiver's relationship to the client, prior training experience, learning preferences, and available time commitment. The caregiver profile data is used to personalize the training curriculum.

At block 682, the method 680 retrieves therapy data for clients associated with the caregiver, including current therapy targets, successful intervention strategies, and recent progress metrics. This therapy data informs the selection and prioritization of training content.

At block 683, the method 680 generates a personalized training curriculum using the large language model. The curriculum comprises a sequence of training modules covering topics such as reinforcement principles, prompting strategies, data collection techniques, and behavior management approaches. Module content is customized based on the specific therapy goals and strategies relevant to the caregiver's associated clients.

At block 684, the method 680 presents training modules to the caregiver via the computing device. Training modules may comprise video-based instruction, interactive simulations, knowledge assessments, and guided practice exercises. The caregiver progresses through modules at their own pace.

At block 685, the method 680 collects caregiver interaction data during module completion, including response accuracy on assessments, time spent on each section, and patterns of interaction. This data is used to assess caregiver learning progress and identify areas requiring additional instruction.

At block 686, the method 680 calculates a caregiver competency score based on assessment performance and engagement metrics. The competency score reflects the caregiver's demonstrated understanding of training content and readiness to implement learned strategies.

At block 687, the method 680 generates updated training recommendations based on the competency score. Recommendations may include additional modules to address competency gaps, refresher content for skills showing decay over time, or advancement to more advanced topics for caregivers demonstrating mastery.

At 688, the method 680 optionally tracks caregiver implementation of trained skills during interactions with clients, correlating implementation fidelity with client progress metrics to provide feedback on the effectiveness of caregiver intervention.

Multi-Source Data Integration for Personalized Therapy (FIG. 7)

Referring now to FIG. 7, an exemplary data flow diagram depicts the integration of multiple data sources 710 for personalized therapy session generation according to an exemplary embodiment. The data integration enables comprehensive client profiling and therapy optimization based on diverse information sources.

The data sources 710 comprise electronic health records (EHR) 712 containing medical history, diagnoses, and prior treatment records; caregiver input interfaces 714 providing observations, concerns, and goals from parents and other caregivers; wearable sensor devices 716 providing continuous physiological and activity data; session recording systems 718 providing video and audio recordings of therapy sessions; and standardized assessments 720 providing norm-referenced evaluation data.

A data integration layer 730 receives data from the multiple data sources 710 and performs data normalization, validation, and transformation. The data integration layer 730 resolves inconsistencies between data sources, handles missing data through imputation or flagging, and converts data to standardized formats for downstream processing.

An AI analysis module 740 processes the integrated data using the trained neural network models to generate comprehensive client profiles, identify patterns and trends, predict therapy needs, and recommend interventions. The AI analysis module 740 continuously updates its analyses as new data becomes available.

A content generation module 750 uses the AI-generated analyses to create personalized therapy content including session plans, interactive activities, and progress visualizations. The content generation module 750 ensures that generated content aligns with client needs, preferences, and therapy goals.

A delivery layer 760 distributes generated content to appropriate devices and users, including client devices for therapy delivery, clinician devices for session management, and caregiver devices for training and progress monitoring.

With continued reference to FIG. 7, engagement level determination logic 765 is described. The engagement level calculation algorithm computes a normalized engagement score E in the range [0.0, 1.0] from multiple sensor inputs according to the following process.

A gaze engagement component Eg is calculated based on eye tracking data. Gaze fixation duration Tfix is measured as the cumulative time in seconds that the client's gaze remains within a defined area of interest (AOI) corresponding to therapy content during a measurement window Tw. The gaze engagement score Eg is calculated using the formula: Eg equals the minimum of 1.0 or the ratio of Tfix divided by Tw. In equation form: Eg=min(1.0, Tfix/Tw). This formula produces a normalized score between 0.0 and 1.0, where higher values indicate greater visual attention to therapy content. For example, if the measurement window Tw is 5 seconds and the client maintains gaze within the AOI for 4 seconds (Tfix=4), then Eg=min(1.0, 4/5)=min(1.0, 0.8)=0.8, indicating strong gaze engagement. If the client looks away frequently and only fixates for 1.5 seconds, then Eg=min(1.0, 1.5/5)=0.3, indicating weak gaze engagement.

A response engagement component Er is calculated based on interaction response patterns. Mean response latency Lmean is calculated as the average time in milliseconds between stimulus presentation and client response over the most recent N trials (typically N=5). Target response latency Ltarget is defined based on task type and client baseline. The response engagement score Er is calculated using the formula: Er equals the maximum of 0.0 or the quantity (1.0 minus the ratio of (Lmean minus Ltarget) divided by Ltarget). In equation form: Er=max(0.0, 1.0−(Lmean−Ltarget)/Ltarget). This formula rewards faster responses and penalizes slower responses relative to the target. For example, if the target response latency Ltarget is 2000 milliseconds and the client's mean response latency Lmean is 1800 milliseconds (faster than target), then Er=max(0.0, 1.0−(1800−2000)/2000)=max(0.0, 1.0−(−200/2000))=max(0.0, 1.0+0.1)=max(0.0, 1.1)=1.0 (capped at maximum). If the client responds more slowly with Lmean of 3000 milliseconds, then Er=max(0.0, 1.0−(3000−2000)/2000)=max(0.0, 1.0−0.5)=0.5, indicating moderate response engagement.

An interaction frequency component Ei is calculated based on the rate of client interactions with the system. Interaction count Nint is the number of valid client interactions (touches, gestures, vocalizations) during measurement window Tw. Expected interaction rate Rexp is defined based on task type (typically 1 interaction per 5 seconds for continuous engagement tasks). Interaction frequency engagement is calculated using the formula: Ei equals the minimum of 1.0 or the ratio of actual interaction rate to expected interaction rate. In equation form: Ei=min(1.0, (Nint/Tw)/Rexp). For example, if the expected interaction rate Rexp is 0.2 interactions per second (1 interaction per 5 seconds), the measurement window Tw is 10 seconds, and the client makes 3 interactions (Nint=3), then the actual rate is 3/10=0.3 interactions per second, and Ei=min(1.0, 0.3/0.2)=min(1.0, 1.5)=1.0 (capped at maximum). If the client makes only 1 interaction in 10 seconds, then Ei=min(1.0, 0.1/0.2)=min(1.0, 0.5)=0.5, indicating moderate interaction engagement.

A physiological arousal component Ep is calculated based on physiological sensor data when available. Heart rate variability (HRV) is calculated as the standard deviation of inter-beat intervals over a 30-second window. Baseline HRV (HRVbase) and task-engaged HRV (HRVtask) ranges are established during calibration. Galvanic skin response (GSR) level is normalized relative to baseline. The physiological engagement score Ep combines normalized HRV and GSR values with equal weighting. In equation form: Ep=0.5 multiplied by normalized HRV plus 0.5 multiplied by normalized GSR, or Ep=0.5*normalize (HRV)+0.5*normalize (GSR). The normalize function maps measured values to the range [0.0, 1.0] based on calibrated baseline and task-engaged ranges. For example, if a client's baseline HRV is 50 milliseconds and their task-engaged HRV is 30 milliseconds, and current HRV measures 35 milliseconds, the normalized HRV would be approximately 0.75 (closer to the engaged state). If normalized GSR is 0.65, then Ep=0.5*0.75+0.5*0.65=0.375+0.325=0.70, indicating moderate-to-high physiological engagement.

The overall engagement level E is calculated as a weighted sum of the component scores. In equation form: E=(Wg multiplied by Eg) plus (Wr multiplied by Er) plus (Wi multiplied by Ei) plus (Wp multiplied by Ep), or E=Wg*Eg+Wr*Er+Wi*Ei+Wp*Ep. The weights Wg, Wr, Wi, and Wp are configurable parameters that sum to 1.0 and can be adjusted based on available sensor modalities and clinical priorities. When all sensors are available, exemplary default weights are Wg=0.35 for gaze, Wr=0.30 for response, Wi=0.20 for interaction, and Wp=0.15 for physiological. For example, if a client has Eg=0.8, Er=0.6, Ei=1.0, and Ep=0.7, then E=0.35*0.8+0.30*0.6+0.20*1.0+0.15*0.7=0.28+0.18+0.20+0.105=0.765, indicating high overall engagement. When physiological sensors are not available, the weight Wp is set to 0 and remaining weights are proportionally increased (for example, Wg=0.41, Wr=0.35, Wi=0.24).

The engagement level E is classified into discrete engagement states for content adaptation purposes: high engagement (E \>=0.7), moderate engagement (0.4 \<=E \<0.7), low engagement (0.2 \<=E \<0.4), and disengaged (E \<0.2). Content adaptation rules are triggered based on engagement state as described in the dynamic difficulty adjustment algorithm.

With continued reference to FIG. 7, a dynamic difficulty adjustment algorithm 770 is described. The dynamic difficulty adjustment algorithm maintains optimal challenge level by adjusting content difficulty in response to client performance and engagement metrics.

At block 780, the algorithm initializes difficulty parameters for a therapy session. Difficulty level D is represented as a scalar value in the range [1, 10], where 1 represents minimum difficulty and 10 represents maximum difficulty. For example, difficulty level 1 might present a simple two-choice discrimination task with unlimited response time, while difficulty level 10 might present a complex multi-step task with strict time limits and multiple distractors. Initial difficulty level D0 is set based on client historical performance data, defaulting to 3 for new clients. A performance history buffer H is initialized to store the most recent N trial outcomes (typically N=10). A difficulty adjustment cooldown timer Tc is initialized to 0.

At block 782, the algorithm presents a therapy task at the current difficulty level D and records the trial outcome. Trial outcome comprises success/failure status, response latency, prompt level required, and engagement level during the trial.

At block 784, the algorithm updates the performance history buffer H with the new trial outcome, removing the oldest entry if the buffer is full.

At block 786, the algorithm calculates performance metrics from the history buffer H. Success rate Rsuccess is calculated as the proportion of successful trials in H (number of successful trials divided by total trials). For example, if the history buffer H contains 10 trials and 7 were successful, then Rsuccess=7/10=0.70, representing a 70% success rate. Mean response latency Lmean is calculated as the average response latency across trials in H. Mean prompt level Pmean is calculated as the average prompt level across trials in H (where 0=independent, 1=gestural prompt, 2=verbal prompt, 3=model prompt, 4=partial physical prompt, 5=full physical prompt). Mean engagement level Emean is calculated as the average engagement level across trials in H.

At block 788, the algorithm determines whether a difficulty adjustment is indicated. If the cooldown timer Tc is greater than 0, no adjustment is made and Tc is decremented. Otherwise, adjustment is evaluated based on the following conditions.

At block 790, if Rsuccess \>0.80 and Pmean \<1.5 and Emean \>0.5, difficulty increase is indicated. This condition represents consistently successful performance with minimal prompting and adequate engagement, suggesting the current difficulty is too easy. Difficulty level D is incremented by 1, capped at maximum difficulty 10. Cooldown timer Tc is set to 3 trials to prevent rapid oscillation.

At block 792, if Rsuccess \<0.60 or Pmean \>3.0 or Emean \<0.3, difficulty decrease is indicated. This condition represents unsuccessful performance, heavy prompting requirements, or low engagement, suggesting the current difficulty is too hard. Difficulty level D is decremented by 1, with minimum value 1. Cooldown timer Tc is set to 3 trials.

At block 794, if neither increase nor decrease condition is met, difficulty remains unchanged. This represents performance within the optimal zone.

At 796, the adjusted difficulty level D is applied to content generation parameters. Difficulty level affects task complexity (number of discriminative stimuli, response requirements), environmental distractors (presence and intensity of visual and auditory distractors), prompt availability (latency before prompts are offered, prompt hierarchy starting level), reinforcement schedule (ratio of reinforced to non-reinforced correct responses), and time limits (duration allowed for responses). Processing returns to block 780 for the next trial.

The dynamic difficulty adjustment algorithm maintains client performance within the optimal zone of approximately 70-80% success rate, which maximizes skill acquisition while maintaining motivation. The algorithm's responsiveness is tunable via the history buffer size N and cooldown timer duration to accommodate different client needs and session formats.

Working Example: Adaptive Street Crossing Training Session

The following working example illustrates operation of the exemplary embodiments in the context of a virtual reality-based street crossing training session for a client with autism spectrum disorder.

A client, referred to as Client A, is a 10-year-old individual with autism who has mastered basic pedestrian safety concepts in tabletop instruction but has not demonstrated generalization to real-world street crossing situations. Client A's therapy goals include independently identifying safe crossing opportunities and executing street crossing procedures without verbal prompting. Client A has a history of distractibility and requires visual supports for multi-step task completion.

Prior to the session, the system retrieves Client A's profile data from the database, including historical performance on pedestrian safety targets (85% accuracy in tabletop discrimination, 40% accuracy in video-based scenarios), identified challenges (difficulty attending to multiple traffic streams simultaneously, delayed response initiation), and successful intervention strategies (visual countdown timers, highlighted attention cues, token reinforcement with access to preferred virtual items).

The AI therapy engine processes Client A's profile data through the trained neural network and generates a personalized session plan. The session plan specifies: initial difficulty level 4 (moderate traffic density, two-lane road, no audio distractors); visual supports including highlighted crosswalk boundaries, traffic light countdown overlay, and attention cue arrows; reinforcement schedule of fixed ratio 3 (FR-3) (reinforcement after every 3 correct responses) with virtual tokens exchangeable for access to a preferred dinosaur exploration environment; session duration of 15 minutes with break opportunity after 8 minutes; and data collection targets including response latency to walk signal, scanning behavior (head movement tracking), and safe crossing execution sequence.

Client A dons the virtual reality headset and begins the session. The system presents a virtual street corner environment with a two-lane road, crosswalk, and pedestrian signal. The first trial presents a scenario where the pedestrian signal changes from "Don't Walk" to "Walk". The system monitors Client A's gaze via eye tracking, detecting that Client A's gaze moves to the pedestrian signal within 1.2 seconds of the change (within acceptable latency). The system monitors head orientation via IMU sensors, detecting left-right scanning movements consistent with checking for traffic. Client A initiates crossing by pressing the controller button 2.3 seconds after signal change and completes crossing along the crosswalk path without deviation.

The behavioral analysis module processes sensor data and classifies the trial as successful: appropriate attention to signal, appropriate scanning behavior, timely response initiation, and safe path execution. Engagement level is calculated as 0.78 (high) based on sustained gaze on task-relevant stimuli, prompt response, and active interaction. The trial outcome is recorded in the performance history buffer. The system delivers reinforcement in the form of a virtual token with celebratory animation and sound effect.

Subsequent trials proceed with varying scenarios. After 5 consecutive successful trials, the dynamic difficulty adjustment algorithm evaluates performance: success rate 100% (5/5), mean prompt level 0.0 (independent), mean engagement 0.75. Because success rate exceeds 0.80 and prompt level is below a prompting threshold, difficulty increase is triggered. Difficulty level increases from 4 to 5, which adds: a third traffic lane, occasional vehicle turning movements, and mild ambient traffic noise.

At the increased difficulty level, Client A encounters a trial with a turning vehicle. Client A initiates crossing appropriately but does not track the turning vehicle, resulting in a simulated near-miss event. The system classifies this as unsuccessful and provides corrective feedback via the virtual clinician avatar, which demonstrates and narrates the scanning behavior required for turning vehicles. Engagement level calculation shows a dip to 0.52 following the failure trial.

Over the next several trials, performance stabilizes at 70% success rate. The dynamic difficulty adjustment algorithm maintains difficulty level 5, as performance is within the optimal zone. The system notes the specific error pattern (failure to track turning vehicles) and generates a recommendation for the supervising clinician to add turning vehicle discrimination as a focused training target.

After 15 minutes, the session concludes. The system generates a session summary report comprising: trials completed: 22; success rate: 72.7%; mean response latency: 2.1 seconds; difficulty progression: level 4 to level 5; tokens earned: 5 (exchanged for 3-minute dinosaur exploration); identified mastery: basic signal response at moderate traffic density; identified targets for additional training: turning vehicle awareness; engagement summary: high engagement (68% of session), moderate engagement (27%), low engagement (5%); and recommendation: continue street crossing training with emphasis on turning vehicle scenarios, consider adding audio distractor tolerance training.

The session data is transmitted to the server computing system, where it is incorporated into Client A's longitudinal progress record. The AI therapy engine updates Client A's skill profile and adjusts recommendations for subsequent sessions. The session summary is transmitted to the supervising clinician's device and Client A's caregiver device for review.

Working Example: Telehealth-Based Discrete Trial Training Session

The following working example illustrates operation of the telehealth platform for delivering discrete trial training via videoconference with AI-assisted data collection and real-time adaptation.

A clinician initiates a telehealth session with Client B, a 6-year-old individual with autism who is working on receptive identification of common objects. The session is conducted via the telehealth platform, with the clinician using a laptop computer and Client B using a tablet computer at home with caregiver present.

Upon session initiation, the system loads Client B's profile and previous session data. The AI therapy engine generates session recommendations: target receptive identification of 5 new food items using a field of 3; use most-to-least prompting hierarchy starting at model prompt level based on previous session performance; reinforcement schedule VR-3 (variable ratio averaging 3 correct responses); present stimuli using on-screen array format with touch response. The clinician reviews recommendations and accepts with one modification: increasing field size to 4 based on recent progress.

During the session, the clinician delivers verbal discriminative stimuli ("Touch cup") while the system presents visual stimulus arrays on Client B's tablet screen. Client B responds by touching stimuli on the touchscreen. The data collection module automatically records: stimulus presented, stimuli in array, client response selection, response latency (measured from end of verbal stimulus to touch response), prompt level delivered, and trial outcome.

The behavioral analysis module processes video feed from Client B's tablet camera using the trained neural network to detect attention, emotional state, and potential interfering behaviors. At trial 8, the system detects Client B looking away from screen for more than 3 seconds and flags potential attention break. The system automatically highlights Client B's video feed for the clinician and suggests an attention redirect procedure.

After 12 trials on the first target (cup), Client B has achieved 10/12 correct responses (83.3%) with mean prompt level 0.8 (between independent and gestural). The system applies mastery criteria (80% or higher across 12 trials with mean prompt level below 1.5) and indicates target mastered. The system automatically advances to the next target (spoon) and logs the mastery event.

During training on subsequent targets, the AI therapy engine detects a pattern: Client B consistently selects stimuli in the upper-left position regardless of target identity when response latency exceeds 4 seconds. The system generates a real-time alert to the clinician suggesting position bias and recommends randomizing stimulus positions more frequently. The clinician acknowledges the recommendation and the system implements increased position randomization.

Following the 25-minute session, the system generates: automated session notes comprising trial-by-trial data, mastery decisions, and prompt level progressions; progress graphs showing acquisition curves for current targets; billing documentation with procedure codes and session duration; and caregiver summary in accessible language describing what was practiced and how caregiver can support generalization. All documentation is automatically populated in the appropriate system records without manual clinician data entry.

Computing Environment

The exemplary embodiments may be implemented on one or more computing devices. A computing device may comprise a desktop computer, laptop computer, tablet computer, smartphone, server computer, virtual machine, or any other device capable of executing software instructions. A computing device comprises at least one processor, at least one memory, at least one storage device, and at least one network interface.

The at least one processor may comprise one or more central processing units (CPUs), one or more graphics processing units (GPUs), one or more tensor processing units (TPUs), one or more neural processing units (NPUs), one or more field-programmable gate arrays (FPGAs), one or more application-specific integrated circuits (ASICs), or combinations thereof. For neural network inference operations, GPU or TPU resources are preferred due to their parallel processing architecture optimized for matrix operations. Exemplary GPU specifications for real-time behavioral analysis include at least 8 GB video memory, at least 5000 CUDA cores or equivalent, and support for FP16 inference acceleration.

The at least one memory comprises volatile memory such as random access memory (RAM), static random access memory (SRAM), or dynamic random access memory (DRAM). Memory capacity for real-time processing should be at least 16 GB to accommodate sensor data buffers, model parameters, and intermediate computation results.

The at least one storage device comprises non-volatile storage such as hard disk drives (HDDs), solid state drives (SSDs), flash memory, optical storage, or cloud-based storage. Storage requirements for the exemplary system include at least 600 GB for trained model files, curriculum content assets, and client data.

Software components executed by computing devices may comprise operating systems, device drivers, runtime environments, application software, machine learning frameworks, and artificial intelligence models. Machine learning frameworks may include TensorFlow (version 2.0 or later), PyTorch (version 1.0 or later), ONNX Runtime for optimized inference, or equivalent frameworks. Models may be exported in ONNX format for cross-platform deployment or in framework-specific formats such as TensorFlow SavedModel or PyTorch TorchScript.

What is claimed is:

1. A computer-implemented method for delivering adaptive therapy for developmental conditions using a parallel processing architecture, the method comprising:

receiving, by at least one processor of a computing system, client-specific data comprising at least one of behavioral assessment data, historical therapy session data, caregiver-reported observations, or skill acquisition metrics;

executing, by the at least one processor, a parallel processing pipeline comprising an ingestion stage, an analysis stage, an adaptation stage, and a rendering stage, each stage executing concurrently on dedicated processor resources;

analyzing, by the analysis stage executing on at least one graphics processing unit or tensor processing unit, the client-specific data using a trained neural network model having an input layer, a plurality of hidden layers, and an output layer to generate a personalized therapy session plan, the trained neural network model computing weighted sums of inputs at each node, applying activation functions to the weighted sums, and propagating activations through the plurality of hidden layers to produce output classifications;

dynamically adjusting, by the adaptation stage executing on the at least one processor, one or more parameters of the personalized therapy session plan in real time based on client performance data collected during execution of a therapy session, the dynamically adjusting comprising modifying at least one of a difficulty level, a prompt intensity, a reinforcement schedule, or an environmental complexity based on comparison of calculated performance metrics against predetermined thresholds;

generating, by the at least one processor, at least one interactive learning module selected from gamified activities, multimedia presentations, or simulated real-world scenarios based on the personalized therapy session plan;

outputting, by the rendering stage executing on the at least one graphics processing unit or tensor processing unit, the at least one interactive learning module for presentation to a client via at least one of an augmented reality display device, a virtual reality display device, or a computing device display;

the parallel processing pipeline maintaining an end-to-end latency of less than 200 milliseconds from receiving the client performance data to outputting an adjusted interactive learning module, thereby enabling behavioral reinforcement contingencies within a time window required for effective behavioral intervention;

capturing, by at least one camera communicatively coupled to the computing system, video data of the client during execution of the therapy session at a frame rate of at least 30 frames per second;

the trained neural network model comprising: a feature extraction module comprising parallel convolutional neural network branches for processing multimodal sensor data, the multimodal sensor data comprising at least two of video frame data, audio waveform data, motion tracking data, or physiological sensor data; a temporal processing module comprising a bidirectional Long Short-Term Memory network that processes concatenated feature vectors from the feature extraction module to capture temporal dynamics across the multimodal sensor data; and a classification module comprising a plurality of fully connected layers that transform output of the temporal processing module into behavioral state classifications; and the dynamically adjusting comprising: calculating an engagement level as a normalized score between 0.0 and 1.0 based on at least one of gaze direction, response latency, or physiological indicators; maintaining a sliding window of at least 10 most recent trial outcomes stored in a first-in-first-out buffer; calculating a success rate as a ratio of successful trials to total trials in the sliding window; increasing the difficulty level when the success rate exceeds 0.80 and a mean prompt level is below 1.5 on a scale from 0 to 5, with 0 representing independent performance and 5 representing full physical prompting; decreasing the difficulty level when the success rate is below 0.60 or the engagement level is below 0.3; and applying a cooldown period of at least 3 trials following each difficulty adjustment to prevent oscillation between difficulty levels.

2. The method of claim 1, further comprising training the trained neural network model using a training dataset comprising autism-specific behavioral samples, the training comprising applying one or more data augmentation transformations to expand the training dataset by a factor of at least 5.

3. The method of claim 2, the one or more data augmentation transformations comprising at least two of: random cropping of video frames; horizontal flipping of video frames; time stretching of audio data by a factor between 0.8 and 1.2; addition of background noise to audio data; random rotation of motion tracking data; or interpolation of physiological data to simulate sensor noise.

4. The method of claim 1, the dynamically adjusting being based on the engagement level calculated from sensor data, the engagement level being calculated based on weighted contributions from gaze data, response data, interaction frequency, and physiological data when available.

5. The method of claim 1, the simulated real-world scenarios comprising at least one of: street crossing simulations with variable traffic patterns, pedestrian behaviors, and environmental distractors rendered in real time; social interaction simulations with virtual characters exhibiting configurable social cues and conversation patterns; restaurant simulations with ordering sequences, payment procedures, and social etiquette scenarios; or public transportation simulations with route planning, fare payment, and passenger interaction scenarios.

6. The method of claim 1, further comprising:

processing the video data using the trained neural network model to detect behavioral indicators comprising at least one of facial expressions, body posture, hand movements, or attention direction; and generating behavioral annotations for the video data based on the detected behavioral indicators, each behavioral annotation comprising a timestamp, a behavioral category selected from a predefined taxonomy, and a confidence score between 0.0 and 1.0.

7. The method of claim 1, further comprising generating, by the at least one processor executing a large language model comprising a transformer architecture with attention mechanisms and feed-forward networks, at least one of: session narrative documentation summarizing therapy activities and client responses in natural language; caregiver guidance materials comprising recommended home practice activities tailored to current therapy targets; or social stories personalized to client therapy targets and interests using client-specific vocabulary and scenarios.

8. The method of claim 1, the personalized therapy session plan targeting at least one skill domain selected from: safety skills comprising street crossing with traffic signal recognition, fire safety with alarm response procedures, and stranger awareness with appropriate response protocols; daily living skills comprising meal preparation with multi-step task sequencing, personal hygiene with routine establishment, and household tasks with organizational strategies; community skills comprising shopping with list management and payment processing, restaurant behavior with ordering and social conventions, and public transportation use with route planning and fare management; or social communication skills comprising greetings with appropriate initiation and response, conversation with turn-taking and topic maintenance, and conflict resolution with de-escalation strategies.

9. A system for providing adaptive therapy for developmental conditions, the system comprising:

at least one server computing device comprising: at least one server processor; at least one graphics processing unit or tensor processing unit; at least one server memory; and at least one server storage device;

a shared memory buffer stored in the at least one server memory and configured to enable concurrent access by the at least one server processor and the at least one graphics processing unit or tensor processing unit;

an ingestion queue stored in the at least one server memory and configured to receive sensor data from a plurality of client computing devices at a rate of at least 60 samples per second;

an analysis buffer stored in the at least one server memory and configured to store neural network inference results comprising behavioral state classifications and confidence scores;

a rendering command queue stored in the at least one server memory and configured to store content adaptation commands for transmission to the plurality of client computing devices;

at least one non-transitory computer-readable storage medium storing instructions that, when executed by the at least one server processor and the at least one graphics processing unit or tensor processing unit, cause the system to:

execute a parallel processing pipeline comprising: an ingestion stage executed by the at least one server processor and configured to read sensor data from the ingestion queue and write processed data to the shared memory buffer; an analysis stage executed by the at least one graphics processing unit or tensor processing unit and configured to read processed data from the shared memory buffer, execute neural network inference using a trained behavioral classification model, and write classification results to the analysis buffer; an adaptation stage executed by the at least one server processor and configured to read the classification results from the analysis buffer, determine content modifications based on the classification results using a rule-based decision engine, and write rendering commands to the rendering command queue; and a rendering stage executed by the at least one graphics processing unit or tensor processing unit and configured to read rendering commands from the rendering command queue and generate updated therapy content; and the parallel processing pipeline maintaining an end-to-end latency of less than 200 milliseconds from sensor data ingestion to rendered content output;

at least one camera communicatively coupled to the at least one server computing device, the at least one camera configured to capture video data of a client during a therapy session at a frame rate of at least 30 frames per second;

the trained behavioral classification model comprising: a feature extraction module comprising parallel convolutional neural network branches for processing multimodal sensor data, the multimodal sensor data comprising at least two of video frame data, audio waveform data, motion tracking data, or physiological sensor data; a temporal processing module comprising a bidirectional Long Short-Term Memory network that processes concatenated feature vectors from the feature extraction module to capture temporal dynamics across the multimodal sensor data; and a classification module comprising a plurality of fully connected layers that transform output of the temporal processing module into behavioral state classifications; and the rule-based decision engine configured to: calculate an engagement level as a normalized score between 0.0 and 1.0 based on at least one of gaze direction, response latency, or physiological indicators; maintain a sliding window of at least 10 most recent trial outcomes stored in a first-in-first-out buffer; calculate a success rate as a ratio of successful trials to total trials in the sliding window; increase a difficulty level when the success rate exceeds 0.80 and a mean prompt level is below 1.5 on a scale from 0 to 5, with 0 representing independent performance and 5 representing full physical prompting; decrease the difficulty level when the success rate is below 0.60 or the engagement level is below 0.3; and apply a cooldown period of at least 3 trials following each difficulty adjustment to prevent oscillation between difficulty levels.

10. The system of claim 9, the shared memory buffer, the ingestion queue, the analysis buffer, and the rendering command queue being configured to enable concurrent read and write access.

11. The system of claim 9, the at least one graphics processing unit or tensor processing unit comprising at least one of: a graphics processing unit having at least 8 GB of video memory and at least 5000 parallel processing cores; the tensor processing unit optimized for matrix multiplication operations used in the neural network inference; or a neural processing unit having dedicated neural network acceleration circuitry with support for quantized integer operations.

12. The system of claim 9, the instructions, when executed, further causing the system to:

calculate an engagement score based on the multimodal sensor data comprising at least two of eye tracking data indicating gaze fixation patterns, response latency data measuring time between stimulus presentation and client response, interaction frequency data measuring client-initiated interactions per unit time, or physiological sensor data measuring autonomic nervous system activity;

classify the engagement score into one of: high engagement when the engagement score is at least 0.7; moderate engagement when the engagement score is at least 0.4 and less than 0.7; low engagement when the engagement score is at least 0.2 and less than 0.4; or disengaged when the engagement score is less than 0.2; and trigger content adaptation when the engagement score classification transitions from a higher engagement state to a lower engagement state.

13. An immersive therapy system comprising:

a head-mounted display device comprising: a display subsystem having a resolution of at least 1440 by 1600 pixels per eye and a refresh rate of at least 72 Hz; and a plurality of integrated sensors comprising at least an eye tracking sensor operating at a rate of at least 90 Hz for capturing gaze direction data with accuracy of 1 degree or better, and an inertial measurement unit operating at a rate of at least 1000 Hz for capturing head orientation and movement data;

a processing unit communicatively coupled to the head-mounted display device, the processing unit comprising at least one central processing unit and at least one graphics processing unit;

at least one non-transitory computer-readable medium storing instructions that, when executed by the processing unit, cause the immersive therapy system to:

receive sensor data from the plurality of integrated sensors at a combined data rate of at least 60 samples per second;

process the received sensor data using a trained neural network model to classify a behavioral state of a client into at least one of attending, responding, waiting, or off-task, the trained neural network model having been trained on autism-specific behavioral data;

generate immersive therapy content based on the classified client behavioral state, the immersive therapy content comprising at least one of augmented reality overlays superimposed on a real-world view or virtual reality environments replacing the real-world view; and dynamically adjust parameters of the immersive therapy content in response to changes in the classified client behavioral state, the parameters comprising at least one of visual complexity, audio characteristics, interaction requirements, or environmental distractors, the dynamically adjusting maintaining an end-to-end latency of less than 200 milliseconds from sensor data capture to content adjustment;

a network interface configured to communicate with a remote server system via a network for receiving therapy session plans and transmitting session data comprising behavioral classifications and performance metrics;

the plurality of integrated sensors further comprising at least one camera configured to capture video data of the client at a frame rate of at least 30 frames per second;

the trained neural network model comprising: a feature extraction module comprising parallel convolutional neural network branches for processing multimodal sensor data, the multimodal sensor data comprising at least two of video frame data, audio waveform data, motion tracking data, or physiological sensor data; a temporal processing module comprising a bidirectional Long Short-Term Memory network that processes concatenated feature vectors from the feature extraction module to capture temporal dynamics across the multimodal sensor data; and a classification module comprising a plurality of fully connected layers that transform output of the temporal processing module into behavioral state classifications; and the dynamically adjusting comprising: calculating an engagement level as a normalized score between 0.0 and 1.0 based on at least one of gaze direction, response latency, or physiological indicators; maintaining a sliding window of at least 10 most recent trial outcomes stored in a first-in-first-out buffer; calculating a success rate as a ratio of successful trials to total trials in the sliding window; increasing a difficulty level when the success rate exceeds 0.80 and a mean prompt level is below 1.5 on a scale from 0 to 5, with 0 representing independent performance and 5 representing full physical prompting; decreasing the difficulty level when the success rate is below 0.60 or the engagement level is below 0.3; and applying a cooldown period of at least 3 trials following each difficulty adjustment to prevent oscillation between difficulty levels.

14. The immersive therapy system of claim 13, the plurality of integrated sensors further comprising at least one of: depth sensors for spatial mapping of a physical environment surrounding the client; cameras for 6-degree-of-freedom position tracking with accuracy of 1 millimeter or better; microphones for voice capture with noise cancellation; or biometric sensors for physiological monitoring including heart rate via photoplethysmography and electrodermal activity via galvanic skin response sensors.

15. The immersive therapy system of claim 13, the instructions, when executed, further causing the immersive therapy system to:

calculate the engagement level as a weighted sum of gaze metrics derived from the eye tracking sensor and physiological metrics derived from biometric sensors, the engagement level being a normalized value between 0.0 and 1.0;

map the engagement level to one of a plurality of engagement states comprising high engagement when the engagement level is at least 0.7, moderate engagement when the engagement level is at least 0.4 and less than 0.7, low engagement when the engagement level is at least 0.2 and less than 0.4, and disengaged when the engagement level is less than 0.2; and trigger content adaptation when the engagement state transitions from a higher engagement state to a lower engagement state.

16. The immersive therapy system of claim 13, further comprising:

a speaker subsystem for audio output of therapy content and feedback; and a haptic feedback subsystem for tactile feedback via vibration motors; and the instructions, when executed, further causing the immersive therapy system to provide multimodal feedback comprising visual feedback via the display subsystem, auditory feedback via the speaker subsystem, and haptic feedback via the haptic feedback subsystem, the multimodal feedback being coordinated with therapy content presentation to reinforce behavioral responses.

17. The immersive therapy system of claim 13, the dynamically adjusting comprising at least one of:

modifying visual complexity of rendered environments by adjusting a number of rendered objects, texture detail level, or lighting complexity based on detected attention levels derived from the eye tracking sensor;

adjusting audio parameters including volume, complexity, and spatial positioning based on detected stress indicators derived from physiological sensors;

changing interaction requirements including response time windows, accuracy thresholds, and prompt levels based on detected fatigue levels; or introducing or removing environmental distractors rendered in the immersive therapy content based on detected mastery levels of targeted skills.

18. The system of claim 9, further comprising:

a videoconferencing module stored on the at least one server storage device and executable by the at least one server processor, the videoconferencing module being configured to establish real-time audiovisual communication sessions between client computing devices and clinician computing devices with latency of less than 150 milliseconds;

a data collection module stored on the at least one server storage device and executable by the at least one server processor, the data collection module being configured to: receive stimulus presentation events and client response events from the client computing devices with timestamps; calculate the response latency as time elapsed between each stimulus presentation event and a corresponding client response event; and store trial data comprising stimulus identity, response identity, the response latency, and outcome in a database stored on the at least one server storage device;

an artificial intelligence therapy engine stored on the at least one server storage device and executable by the at least one server processor and the at least one graphics processing unit or tensor processing unit, the artificial intelligence therapy engine comprising the trained behavioral classification model and being configured to: analyze patterns in stored trial data to detect response biases including position bias and stimulus preference bias; and generate real-time recommendations for session modifications based on detected biases; and a reporting module stored on the at least one server storage device and executable by the at least one server processor, the reporting module being configured to generate progress reports comprising acquisition curves showing skill development over time, mastery determinations based on predetermined criteria, and billing documentation with procedure codes.

19. The system of claim 18, the data collection module being further configured to:

automatically record therapy session video with synchronized behavioral annotations indicating detected behavioral events;

detect discrete trial training structure from video analysis comprising stimulus delivery timing, client response timing, and consequence delivery timing; and calculate inter-observer agreement metrics by comparing automated annotations generated by the artificial intelligence therapy engine with clinician-entered data to validate annotation accuracy.

20. The system of claim 18, the artificial intelligence therapy engine being further configured to:

identify skill acquisition patterns across a plurality of clients stored in the database to detect effective teaching procedures for specific skill types;

recommend evidence-based interventions based on a client behavioral profile and historical response patterns stored in the database; and predict time to mastery for targeted skills based on a current learning trajectory calculated from the trial data in the database.

21. The system of claim 18, further comprising an integration module stored on the at least one server storage device and executable by the at least one server processor, the integration module being configured to:

exchange data with external electronic health record systems using at least one of Health Level Seven protocol or Fast Healthcare Interoperability Resources protocol;

generate billing codes based on documented therapy activities in compliance with Current Procedural Terminology standards; and synchronize client data with school-based intervention systems via secure data exchange protocols.

22. The method of claim 1, further comprising training caregivers of individuals receiving the adaptive therapy, the training comprising:

receiving, by the at least one processor, caregiver profile data comprising caregiver role information identifying relationship to the client, prior training history indicating completed training modules, and learning preferences indicating preferred content modalities;

receiving, by the at least one processor, client therapy data comprising current therapy targets specifying skills being addressed, successful intervention strategies that have produced skill acquisition, and recent progress metrics quantifying performance trends;

generating, by the at least one processor executing a large language model, a personalized training curriculum comprising a sequence of training modules selected and ordered based on the caregiver profile data and the client therapy data;

presenting, via a computing device communicatively coupled to the at least one processor, at least one interactive training module from the personalized training curriculum, the at least one interactive training module comprising at least one of video-based instruction demonstrating intervention techniques, interactive simulation allowing practice of techniques, knowledge assessment measuring comprehension, or guided practice exercise with feedback;

collecting caregiver interaction data during completion of the at least one interactive training module, the caregiver interaction data comprising response accuracy on assessments, time spent on each module section, and interaction patterns indicating engagement;

calculating a caregiver competency score based on the caregiver interaction data and performance on knowledge assessments, the caregiver competency score being a normalized value between 0.0 and 1.0; and generating updated training recommendations based on the caregiver competency score, the updated training recommendations comprising at least one of additional modules for identified competency gaps, refresher content for skills showing decay over time, or advancement to more advanced topics upon demonstrated mastery.

23. The method of claim 22, further comprising:

tracking caregiver engagement with training materials over time by recording login frequency, module completion rates, and time spent in training;

correlating caregiver training completion with client progress metrics to identify relationships between caregiver competency and client outcomes;

generating effectiveness reports comparing client outcomes for caregivers who have completed training versus caregivers who have not completed training; and automatically scheduling refresher training based on time elapsed since initial training and detected skill decay indicators derived from caregiver assessment performance.

24. A non-transitory computer-readable medium storing instructions that, when executed by at least one processor communicatively coupled to at least one graphics processing unit, cause the at least one processor and the at least one graphics processing unit to:

receive multimodal sensor data from a head-mounted display device worn by a client during a therapy session, the multimodal sensor data comprising eye tracking data captured at a rate of at least 90 Hz indicating gaze direction and pupil dilation, inertial measurement data captured at a rate of at least 1000 Hz indicating head orientation and movement, and video data captured at a rate of at least 30 frames per second depicting the client;

process the multimodal sensor data using a trained neural network model executed on the at least one graphics processing unit to calculate an engagement score, the trained neural network model comprising: a feature extraction module that processes each sensor modality using a dedicated neural network branch to produce modality-specific feature vectors; a fusion module that concatenates the modality-specific feature vectors to produce a combined feature vector; and a classification module that processes the combined feature vector to produce engagement level predictions as a normalized score between 0.0 and 1.0;

classify the engagement score into one of a plurality of engagement states comprising high engagement when the engagement score is at least 0.7, moderate engagement when the engagement score is at least 0.4 and less than 0.7, low engagement when the engagement score is at least 0.2 and less than 0.4, and disengaged when the engagement score is less than 0.2;

determine, based on the classified engagement state, at least one content adaptation comprising modifying a difficulty level on a scale of 1 to 10, adjusting environmental complexity by adding or removing rendered objects, or changing reinforcement parameters including reward timing and magnitude;

transmit the at least one content adaptation to the head-mounted display device within 200 milliseconds of capture of the multimodal sensor data;

store session data in at least one storage device, the session data comprising engagement state transitions with timestamps, content adaptations applied, and client responses recorded, for subsequent analysis to improve future therapy sessions;

the trained neural network model comprising: a feature extraction module comprising parallel convolutional neural network branches for processing the multimodal sensor data, the multimodal sensor data comprising at least two of video frame data, audio waveform data, motion tracking data, or physiological sensor data; a temporal processing module comprising a bidirectional Long Short-Term Memory network that processes concatenated feature vectors from the feature extraction module to capture temporal dynamics across the multimodal sensor data; and a classification module comprising a plurality of fully connected layers that transform output of the temporal processing module into behavioral state classifications; and the determining comprising: calculating an engagement level as a normalized score between 0.0 and 1.0 based on at least one of gaze direction, response latency, or physiological indicators; maintaining a sliding window of at least 10 most recent trial outcomes stored in a first-in-first-out buffer; calculating a success rate as a ratio of successful trials to total trials in the sliding window; increasing a difficulty level when the success rate exceeds 0.80 and a mean prompt level is below 1.5 on a scale from 0 to 5, with 0 representing independent performance and 5 representing full physical prompting; decreasing the difficulty level when the success rate is below 0.60 or the engagement level is below 0.3; and applying a cooldown period of at least 3 trials following each difficulty adjustment to prevent oscillation between difficulty levels.

25. The non-transitory computer-readable medium of claim 24, the instructions further causing the at least one processor to:

analyze stored session data to identify patterns in engagement state transitions including common triggers for disengagement and effective re-engagement interventions;

correlate engagement patterns with therapy content characteristics to determine content features associated with high engagement for the client;

generate recommendations for therapy session modifications based on the identified patterns and correlations; and update therapy session plans for future sessions based on the generated recommendations to optimize engagement and skill acquisition.

26. The system of claim 9, further comprising:

a plurality of client computing devices communicatively coupled to the at least one server computing device via a network, at least one client computing device of the plurality comprising a head-mounted display device with integrated eye tracking operating at a rate of at least 90 Hz;

a telehealth module stored on the at least one server storage device and executable by the at least one server processor, the telehealth module being configured to coordinate therapy sessions delivered via the plurality of client computing devices, the coordinating comprising scheduling sessions, establishing real-time video-conferencing with latency of less than 150 milliseconds, and managing session state;

a content generation module stored on the at least one server storage device and executable by the at least one server processor, the content generation module being configured to generate personalized therapy content using trained artificial intelligence models stored on the at least one server storage device, the personalized therapy content comprising parameterized learning modules with at least 10 adjustable difficulty levels; and a data analytics module stored on the at least one server storage device and executable by the at least one server processor, the data analytics module being configured to: aggregate behavioral data collected from the plurality of client computing devices into a unified data store; process the aggregated behavioral data using the trained behavioral classification model executed on the at least one graphics processing unit or tensor processing unit to identify behavioral patterns and predict therapy needs; and generate therapy optimization recommendations based on the identified patterns and predictions.

27. The system of claim 26, the data analytics module being further configured to:

perform cross-client analysis on the unified data store to identify intervention strategies that are effective across a plurality of clients with similar behavioral profiles;

generate population-level insights regarding therapy effectiveness for different diagnostic subtypes based on aggregated outcome data; and provide clinician decision support by presenting comparative outcome data for alternative intervention approaches based on the cross-client analysis.

* * * * *